United States Patent [19]
Coy et al.

[11] Patent Number: 5,877,277
[45] Date of Patent: Mar. 2, 1999

[54] OCTAPEPTIDE BOMBESIN ANALOGS

[75] Inventors: David H. Coy, New Orleans, La.; Jacques-Pierre Moreau, Upton; Sun Hyuk Kim, Chestnut Hill, both of Mass.

[73] Assignees: Biomeasure, Inc., Hopkington, Mass.; Administrators of the Tulane Educational Fund, New Orleans, La.

[21] Appl. No.: 337,127

[22] Filed: Nov. 10, 1994

Related U.S. Application Data

[63] Continuation of Ser. No. 779,039, Oct. 18, 1991, abandoned, which is a continuation-in-part of Ser. No. 502,438, Mar. 30, 1990, Pat. No. 5,084,555, which is a continuation-in-part of Ser. No. 397,169, Aug. 21, 1989, abandoned, which is a continuation-in-part of Ser. No. 376,555, Jul. 7, 1989, abandoned, which is a continuation-in-part of Ser. No. 317,941, Mar. 2, 1989, abandoned, which is a continuation-in-part of Ser. No. 282,328, Dec. 9, 1988, Pat. No. 5,162,497, which is a continuation-in-part of Ser. No. 257,998, Oct. 14, 1988, abandoned, which is a continuation-in-part of Ser. No. 248,771, Sep. 23, 1988, abandoned, which is a continuation-in-part of Ser. No. 207,759, Jun. 16, 1988, abandoned, which is a continuation-in-part of Ser. No. 204,171, Jun. 8, 1988, abandoned, which is a continuation-in-part of Ser. No. 173,311, Mar. 25, 1988, abandoned, which is a continuation-in-part of Ser. No. 100,571, Sep. 24, 1987, abandoned.

[51] Int. Cl.$^6$ ............... C07K 5/00; C07K 7/00; C07K 7/06; A61K 38/00
[52] U.S. Cl. ............................ 530/328; 530/323
[58] Field of Search ...................... 530/328, 323

[56] References Cited

U.S. PATENT DOCUMENTS

| | | |
|---|---|---|
| 4,207,311 | 6/1980 | Brown et al. . |
| 4,737,487 | 4/1988 | Watts et al. ............................ 514/15 |
| 4,803,261 | 2/1989 | Coy et al. . |
| 5,068,222 | 11/1991 | Gambel et al. ........................ 514/15 |
| 5,084,555 | 1/1992 | Coy et al. ............................ 530/328 |
| 5,162,497 | 11/1992 | Coy et al. ............................ 530/314 |
| 5,217,955 | 6/1993 | Bogden et al. ........................ 514/12 |

FOREIGN PATENT DOCUMENTS

| | | |
|---|---|---|
| 0 309 297 A2 | 3/1989 | European Pat. Off. . |
| 0 345 990 | 5/1989 | European Pat. Off. . |
| 9003980 | 4/1990 | WIPO . |

OTHER PUBLICATIONS

Camble et al., Peptides: Chemistry, Structure and Biology "ICI 216140 and other potent in vivo antagonist analogs of bombesin/gastrin–releasing peptide" 174–176, 1990.

Heimbrook et al., Peptides: Chemistry, Structure and Biology "Design and evaluation of novel gastrin–releasing peptide antagonists for the treatment of small cell lung cancer" 56–59, 1990.

Rudinger, Peptide Hormones, Parsons (Ed.), U Park Press, Baltimore, pp. 1–7 (1976).

Coy et al., J. Biol. Chem, vol. 264(25) pp. 14691–14697 (Sep. 1989).

Broccardo et al., Br. J. Pharmac vol. 55, pp. 221–227 (1975).

Cram et al., Organic Chemistry, 2nd Edition, McGraw–Hill Book Company, New York, pp. 607–613 (1964).

*Primary Examiner*—Avis M. Davenport
*Attorney, Agent, or Firm*—Fish & Richardson P.C.

[57] ABSTRACT

A linear (i.e., non-cyclic) analog of biologically active amphibian bombesin, mammalian gastrin-releasing peptide (GRP), or mammalian growth hormone releasing factor (GRF), having an active site and a binding site responsible for the binding of the peptide to a receptor on a target cell. Cleavage of a peptide bond in the active site of naturally occurring bombesin, GRP, or GRF is unnecessary for in vivo biological activity. The analog has one of the following modifications: (a) a deletion of an amino acid residue within the active site and a modification of an amino acid residue outside of the active site, (b) a replacement of two amino acid residues within the active site with a synthetic amino acid, a β-amino acid, or a γ-amino acid residue, or (c) a non-peptide bond instead of a peptide bond between an amino acid residue of the active site and an adjacent amino acid residue.

5 Claims, 4 Drawing Sheets

OCTAPEPTIDE BOMBESIN ANALOGS

This application is a continuation application of Ser. No. 07/779,039 filed Oct. 18, 1991, now abandoned; which is a continuation-in-part of Ser. No. 07/502,438, filed Mar. 30, 1990, now U.S. Pat. No. 5,084,555; which is a continuation-in-part of Ser. No. 07/397,169, filed Aug. 21, 1989, now abandoned; which is a continuation-in-part of Ser. No. 376,555, filed Jul. 7, 1989, now abandoned; which is a continuation-in-part of Ser. No. 07/317,941, filed Mar. 2, 1989, now abandoned; which is a continuation-in-part of Ser. No. 07/282,328, filed Dec. 9, 1988, now U.S. Pat. No. 5,162,497; which is a continuation-in-part of Ser. No. 07/257,998, filed Oct. 14, 1988, now abandoned; which is a continuation-in-part of Ser. No. 07/248,771, filed Sep. 23, 1988, now abandoned; which is a continuation-in-part of Ser. No. 07/207,759, filed Jun. 16, 1988, now abandoned; which is a continuation-in-part of Ser. No. 07/204,171, filed Jun. 8, 1988, now abandoned; which is a continuation-in-part of Ser. No. 07/173,311, filed Mar. 25, 1988, now abandoned; which is a continuation-in-part of Ser. No. 07/100,571, filed Sep. 24, 1987, now abandoned.

BACKGROUND OF THE INVENTION

This invention relates to therapeutic peptides useful, e.g., for treatment of benign or malignant proliferation of tissue, for gastrointestinal disorders, and for diabetes.

The amphibian peptide bombesin, pGlu—Gln—Arg—Leu—Gly—Asn—Gln—Trp—Ala—Val—Gly—His—Leu—Met—$NH_2$ (SEQ ID NO: 1) (Anastasi et al., Experientia 27:166–167 (1971)), is closely related to the mammalian gastrin-releasing peptides (GRP), e.g., the porcine GRP, $H_2N$—Ala—Pro—Val—Ser—Val—Gly—Gly—Gly—Thr—Val—Leu—Ala—Lys—Met—Tyr—Pro—Arg—Gly—Asn—His—Trp—Ala—Val—Gly—His—Leu—Met—($NH_2$) (SEQ ID NO: 2) (McDonald et al., Biochem. Biophys. Res. Commun. 90:227–233 (1979)) and human GRP, $H_2N$—Val—Pro—Leu—Pro—Ala—Gly—Gly—Gly—Thr—Val—Leu—Thr—Lys—Met—Tyr—Pro—Arg—Gly—Asn—His—Trp—Ala—Val—Gly—His—Leu—Met ($NH_2$)(SEQ ID NO: 3). Bombesin has been found to be a growth factor for a number of human cancer cell lines, including small-cell lung carcinoma (SCLC), and has been detected in human breast and prostate cancer (Haveman et al., eds. *Recent Results in Cancer Research—Peptide Hormones in Lung Cancer*, Springer-Verlag, New York:1986). A number of these cancers are known to secrete peptide hormones related to GRP or bombesin. Consequently, antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice (Cuttitta et al., Cancer Survey 4:707–727 (1985)). In 3T3 murine fibroblasts which are responsive to the mitotic effect of bombesin, Zachary and Rozengurt observed that a substance P antagonist (Spantide) acted as a bombesin antagonist (Zachary et al., Proc. Natl. Acad. Sci. (USA), 82:7616–7620 (1985)). Heinz-Erian et al. replaced His at position 12 in bombesin with D—Phe and observed bombesin antagonist activity in dispersed acini from guinea pig pancreas (Heinz-Erian et al., Am. J. of Physiol. 252:G439–G442 (1987)). Rivier reported work directed toward restricting the conformational freedom of the bioactive C-terminal decapeptide of bombesin by incorporating intramolecular disulfide bridges; however, Rivier mentioned that, so far, bombesin analogs with this modification fail to exhibit any antagonist activity (Rivier et al., "Competitive Antagonists of Peptide Hormones," in Abstracts of the International Symposium on Bombesin-Like Peptides in Health and Disease, Rome, Italy (October, 1987).

Abbreviations (uncommon):

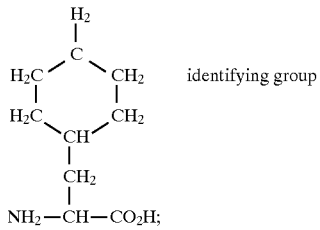

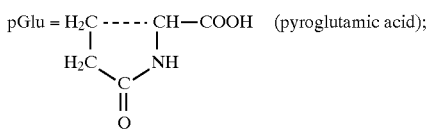

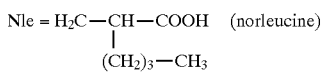

Pal=3-pyridyl-alanine

β-leu=β-homoleucine

γ-leu=gamma-homoleucine

D-Cpa=D-p-chlorophenylalanine

HyPro=hydroxyproline

Nal=naphthylalanine

Sar=sarcosine $F_5$-Phe=penta-fluoro-Phenylalanine

Sta (statine)=(3S, 4S)-4-amino-3-hydroxy-6-methylheptanoic acid, and has the chemical structure:

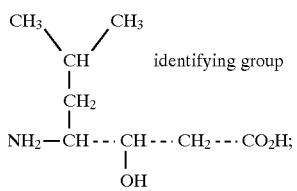

AHPPA=(3S,4S)-4-amino-3-hydroxy-5-phenylpentanoic acid, and has the chemical structure:

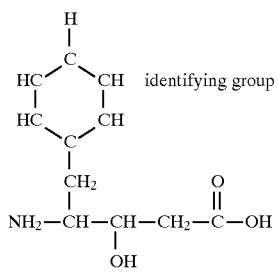

ACHPA=(3S, 4S)-4-amino-5-cyclohexyl-3-hydroxypentanoic acid and has the chemical structure:

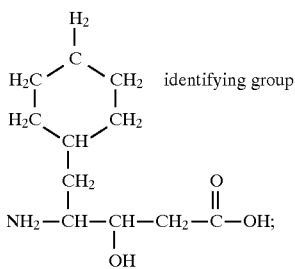

R=right (D) configuration;
S=left (L) configuration;
racemate=equal mix of R and S
1-methyl-His;
3-methyl-His=methyl ($CH_3$) group on nitrogen at positions 1 or 3 of Histidine:

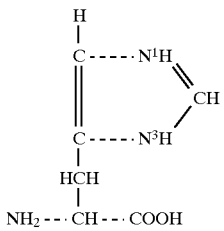

SUMMARY OF THE INVENTION

In general, the invention features a linear (i.e., non-cyclic) analog of biologically active mammalian gastrin-releasing peptide (GRP), amphibian bombesin, or mammalian growth hormone releasing factor (GRF) having an active site and a binding site responsible for the binding of the peptide to a receptor on a target cell; cleavage of a peptide bond in the active site of naturally occurring bombesin, GRP, or GRF is unnecessary for in vivo biological activity. The analog has one of the following modifications: (a) a deletion of an amino acid residue within the active site and a modification of an amino acid residue outside of the active site, (b) a replacement of two amino acid residues within the active site with a synthetic amino acid, e.g., statine, AHPPA, or ACHPA, a β-amino acid, or a γ-amino acid residue, or (c) a non-peptide bond instead of a peptide bond between an amino acid residue of the active site and an adjacent amino acid residue.

In preferred embodiments the analog is capable of acting as a competitive inhibitor of the naturally occurring peptide by binding to the receptor and, by virtue of one of the modifications, failing to exhibit the in vivo biological activity of the naturally occurring peptide.

The locations of the modifications that give rise to antagonists are determined by the location of the active site in the naturally occuring peptide. For example, the linear peptides for which introduction of a non-peptide bond between the carboxyl terminal and adjacent amino acid residues, or the replacement of the natural carboxyl terminal and adjacent amino acid residues with a synthetic, β-, or γ-amino acid residue, or the deletion ("des") of the C-terminal amino acid residue are useful in creating or enhancing antagonist activity are those in which activity is associated with the two C-terminal amino acid residues of the amino acid chain. Similarly, where the active site is located in the amino terminal portion of the naturally occuring peptide, the corresponding analogs of the invention will possess modifications in their amino terminal portions.

In preferred embodiments the active site includes at least one amino acid residue located in the carboxyl terminal half of the naturally occurring biologically active peptide and that amino acid residue is located in the carboxyl terminal half of the linear peptide.

In preferred embodiments the binding sites includes at least one amino acid residue located in the amino terminal half of the naturally occurring biologically active peptide and that amino acid residue is located in the amino terminal half of the linear peptide.

Modifications can be introduced in a region involved in receptor binding, or in a non-binding region. Preferably, analogs of the invention are 25% homologous, most preferably, 50% homologous, with the naturally occurring peptides.

The analogs of the invention may have one of the modifications given in the generic formula given below; either a non-peptide bond instead of a peptide bond between an amino acid residue of the active site and an adjacent amino acid residue; or a synthetic amino acid, e.g. a statine, an AHPPA, or an ACHPA, a β-amino acid, or a γ-amino acid residue in place of two natural amino acid residues; or a deletion of the C-terminal amino acid residue, accompanied by the addition of a substituent on the actual C-terminal group and the presence of an N-terminal residue that is not the natural N-terminal amino acid residue of the peptides from which the analogs are derived. (Statine, AHPPA, and ACHPA have the chemical structures defined above. Where statine is used herein, AHPPA or ACHPA may also be used.)

By non-peptide bond is meant that the carbon atom participating in the bond between two residues is reduced from a carbonyl carbon to a methylene carbon, i.e., $CH_2$—NH; or, less preferably that CO—NH is replaced with any of $CH_2$—S, $CH_2$—O, $CH_2$—$CH_2$, $CH_2$—CO, or CO—$CH_2$. (A detailed discussion of the chemistry of non-peptide bonds is given in Coy et al. (1988) Tetrahedron 44,3:835–841, hereby incorporated by reference, Tourwe (1985) Janssen Chim. Acta 3:3–15, 17–18, hereby incorporated by reference, and Spatola (1983) in Chemistry and Biochemistry of Amino Acids, Peptides, and Proteins, (B. Weinstein, ed.) M. Dekker, New York and Basel, pp. 267–357, hereby incorporated by reference.)

One modification of the naturally occurring peptide to create an antagonist is of the amino terminal end of the molecule, such as those described for the amino terminal positions in the generic formula below; for example, the N-terminal amino acid residue, which is $A^0$ or, if $A^0$ is deleted, is $A^1$ or, if $A^0$ and $A^1$ are deleted, is $A^2$ below, may be an aromatic D-isomer, or may be an alkylated amino acid residue. (Where "D" is not designated as the configuration of an amino acid, L is intended.)

The therapeutic peptide includes between seven and ten amino acid residues, inclusive, and is an analog of one of the following peptides terminating at the carboxy-terminus with a Met residue: (a) litorin; (b) the ten amino acid carboxy-terminal region of mammalian GRP; and (c) the ten amino acid carboxy-terminal region of amphibian bombesin. The therapeutic peptide is of the following formula:

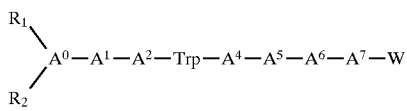

wherein
- $A^0$=pGlu, Gly, Nle, α-aminobutyric acid, or the D-isomer of any of Ala, Val, Gln, Asn, Leu, Ile, Met, p—X—Phe (where X=F, Cl, Br, $NO_2$, OH, H or $CH_3$), Trp, Cys, or β-Nal, or is deleted;
- $A^1$=the D or L-isomer of any of pGlu, Nle, α-aminobutyric acid, or the D-isomer of any of Ala, Val, Gln, Asn, Leu, Ile, Met, p—X—Phe (where X=F, Cl, Br, $NO_2$, OH, H or $CH_3$), $F_5$—Phe, Trp, Cys, or β-Nal, or is deleted;
- $A^2$=pGlu, Gly, Ala, Val, Gln, Asn, Leu, Ile, Met, p-X—Phe (where X=F, Cl, Br, $NO_2$, OH, H or $CH_3$), Trp, Cys, β-Nal, His, 1-methyl-His, or 3-methyl-His;
- $A^4$=Ala, Val, Gln, Asn, Gly, Leu, Ile, Nle, α-aminobutyric acid, Met, p-X—Phe (where X=F, Cl, Br, $NO_2$, OH, H or $CH_3$), Trp, Cys, or β-Nal;
- $A^5$=Gln, Asn, Gly, Ala, Leu, Ile, Nle, α-aminobutyric acid, Met, Val, p-X—Phe (where X=F, Cl, Br, OH, H or $CH_3$), Trp, Thr, or β-Nal;
- $A^6$=Sar, Gly, or the D-isomer of any of Ala, N-methyl-Ala, Val, Gln, Asn, Leu, Ile, Met, p-X—Phe (where X=F, Cl, Br, $NO_2$, OH, H or $CH_3$), Trp, Cys, or β-Nal;
- $A^7$=1-methyl-His, 3-methyl-His, or His;

provided that, if $A^0$ is present, $A^1$ cannot be pGlu; further provided that, if $A^0$ or $A^1$ is present, $A^2$ cannot be pGlu; further provided that, when $A^0$ is deleted and $A^1$ is pGlu, $R_1$ must be H and $R_2$ must be the portion of Glu that forms the imine ring in pGlu; and further provided that, W can be any one of the following:

(I):

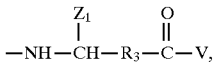

wherein $R_3$ is $CHR_{20}$—$(CH_2)_{n1}$ (where $R_{20}$ is either of H or OH; and n1 is either of 1 or 0), or is deleted, and $Z_1$ is the identifying group of any of the amino acids Gly, Ala, Val, Leu, Ile, Ser, Asp, Asn, Glu, Gln, p-X—Phe (where X=H, F, Cl, Br, $NO_2$, OH, or $CH_3$), $F_5$—Phe, Trp, Cys, Met, Pro, HyPro, cyclohexyl-Ala, or β-nal; and V is either $OR_4$, or

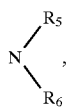

where $R_4$ is any of $C_{1-20}$ alkyl, $C_{3-20}$ alkenyl, $C_{3-20}$ alkinyl, phenyl, naphthyl, or $C_{7-10}$ phenylalkyl, and each $R_5$, and $R_6$, independently, is any of H, $C_{1-12}$ alkyl, $C_{7-10}$ phenylalkyl, lower acyl, or,

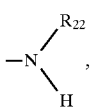

where $R_{22}$ is any of H, $C_{1-12}$ alkyl, $C_{7-10}$ phenylalkyl, or lower acyl; provided that, when one of $R_5$ or $R_6$ is —$NHR_{22}$, the other is H;

(II):

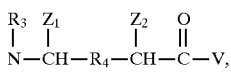

wherein $R_4$ is $CH_2$—NH, $CH_2$—S, $CH_2$—O, CO—$CH_2$, $CH_2$—CO, or $CH_2$—$CH_2$, and each $Z_1$ and $Z_2$, independently, is the identifying group of any one of the amino acids Gly, Ala, Val, Leu, Ile, Ser, Asp, Asn, Glu, Gln, β-Nal, p-X—Phe (where X=H, F, Cl, Br, $NO_2$, OH or $CH_3$), $F_5$—Phe, Trp, Cys, Met, Pro, HyPro, or cylcohexyl-Ala; and V is either $OR_5$ or

where each $R_3$, $R_5$, $R_6$, and $R_7$, independently, is H, lower alkyl, lower phenylalkyl, or lower naphthylalkyl;

(III):

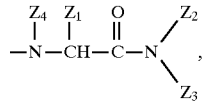

wherein $Z_1$ is the identifying group of any one of the amino acids Gly, Ala, Val, Leu, Ile, Ser, Asp, Asn, Glu, β-Nal, Gln, p-X—Phe (where X=H, F, Cl, Br, $NO_2$, OH or $CH_3$), $F_5$—Phe, Trp, Cys, Met, Pro, or HyPro; and each $Z_2$, $Z_3$, and $Z_4$, independently, is H, lower alkyl, lower phenylalkyl, or lower naphthylalkyl; or (IV):

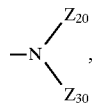

wherein each $Z_{20}$ and $Z_{30}$, independently, is H, lower alkyl, lower phenylalkyl, lower naphthylalkyl; further provided that, when either of $Z_{20}$ or $Z_{30}$ is other than H, $A^7$ is His, $A^6$ is Gly, $A^5$ is Val, $A^4$ is Ala, $A^2$ is His, and either of $R_1$ or $R_2$ is other than H, $A^1$ must be other than deleted; further provided that, for the formulas (I) through (IV), any asymmetric carbon atom can be R, S or a racemic mixture; and further provided that each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkinyl, phenyl, naphthyl, or $C_{7-10}$ phenylalkyl), or lower acyl, and $R_1$ and $R_2$ are bonded to the N-terminal amino acid of said peptide, and further provided that when one of $R_1$ or $R_2$ is $COE_1$, the other must be H, or a pharmaceutically acceptable salt thereof.

Preferably, the amino acid sequence of the therapeutic peptide of the generic formula (id) is at least 25% homologous with the amino acid sequence of the naturally occurring peptide; most preferably, this homology is at least 50%.

More preferably, in the generic formula above,
- $A^0$=Gly, D-Phe, or is deleted;
- $A^1$=p-Glu, D-Phe, D-Ala, D-β-Nal, D-Cpa, or D-Asn;
- $A^2$=Gln, His, 1-methyl-His, or 3-methyl-His;
- $A^4$=Ala;
- $A^5$=Val;
- $A^6$=Sar, Gly, D-Phe, or D-Ala;

$A^7$=His; and and, where W is (I) and $R_3$ is $CH_2$ or $CH_2$—$CH_2$, $Z_1$ is the identifying group of Leu or Phe, where W is (I) and $R_3$ is CHOH—$CH_2$, $Z_1$ is the identifying group of Leu, cyclohexyl-Ala, or Phe and each $R_5$ and $R_6$ is H, and where W is (I), V is $NHR_6$, and $R_6$ is $NH_2$; where W is (II) and $R_4$ is $CH_2$—NH each $Z_1$ is the identifying group of Leu, or Phe, and $Z_2$ is the identifying group of Leu or Phe; where W is (III), $Z_1$ is the identifying group of any one of the amino acids Leu or p-X—Phe (where X=H, F, Cl, Br, $NO_2$, OH or $CH_3$); and each $Z_2$, $Z_3$ and $Z_4$, independently, is H, lower alkyl, lower phenylalkyl, or lower naphthylalkyl; and where W is (IV), each $Z_{20}$ and $Z_{30}$, is H; and each $R_1$ and $R_2$, independently, is H, lower alkyl, or lower acyl.

Preferred peptides include those in which W is (II), $R_4$ is $CH_2$—NH, and the carbon atom bonded to $Z_2$ is of the R configuration.

Examples of preferred bombesin or GRP peptides are:

D-β-Nal—Gln—Trp—Ala—Val—Gly—His—LeuΨ[$CH_2NH$]Phe—$NH_2$,

D-Phe—Gln—Trp—Ala—Val—Gly—His—Leu—ethylamide, p-Glu—Gln—Trp—Ala—Val—Gly—His—statine-amide, (SEQ ID NO: 4)

D-Phe—Gln—Trp—Ala—Val—Gly—His—LeuΨ[$CH_2NH$]-D-Phe—$NH_2$,

D-Cpa—Gln—Trp—Ala—Val—Gly—His-β-Leu—$NH_2$,

D-Cpa—Gln—Trp—Ala—Val—D—Ala—His-β-Leu—$NH_2$,

D-Cpa—Gln—Trp—Ala—Val—Gly—His—LeuΨ[$CH_2NH$]—Phe—$NH_2$.

In another preferred embodiment, W is (I), V is $OR_4$, $R_4$ can be any substituent provided in (I) of the generic formula (id), and $A^6$ is N-methyl-D-Ala, i.e., a preferred peptide contains both a carboxy terminal ester component in combination with N-methyl-D-Ala, in position $A^6$; or D-$F_5$—Phe in position $A^1$.

Examples of preferred peptides are

D-Phe—Gln—Trp—Ala—Val—N-methyl-D-Ala—His—Leu-methylester,

D-$F_5$—Phe—Gln—Trp—Ala—Val—D—Ala—His—Leu-methylester,

D-$F_5$—Phe—Gln—Trp—Ala—Val—D—Ala—His—Phe-methylester,

D-$F_5$—Phe—Gln—Trp—Ala—Val—Gly—His—Phe-methylester, and

D-$F_5$—Phe—Gln—Trp—Ala—Val—Gly—His—Leu-methylester.

An example of a preferred GRF peptide of the invention is

Tyr—Ala²—Asp—Ala—Ile—Phe—Thr—Asn—SerΨ[$CH_2NH$]Tyr—Arg—Lys—Val—Leu—Gly—Gln—Leu—Ser—Ala—Arg—Lys—Leu—Leu—Gln—Asp—Ile—Met—Ser—Arg—$NH_2$; (SEQ ID NO: 5); most preferably, the peptide contains, D-Ala, N-methyl-D-Ala, or a-aminobutyric acid in position 2. (Non-peptide bonds in which the peptide bond is reduced are symbolized herein by "Ψ[$CH_2NH$]" or "Ψ".)

Other preferred peptide analogs with an ester C terminus are of the following formula:

$A^1$—Gln—Trp—Ala—Val—$A^6$—His—$A^8$—O—R, wherein $A^1$ is the D- or L-isomer of p—Glu; $A^6$ is Gly or D—Ala; $A^8$ is Phe or Leu; and R is $C_1$-$C_4$ alkyl or $C_7$-$C_{14}$ phenylalkyl. Among these analogs, p-Glu—Gln—Trp—Ala—Val—D—Ala—His—Phe-Methylester, p-Glu—Gln—Trp—Ala—Val—Gly—His—Phe-Methylester (SEQ ID NO. 8), p-Glu—Gln—Trp—Ala—Val—Gly—His—Leu-Methylester (SEQ ID NO. 9), and p—Glu—Gln—Trp—Ala—Val—D—Ala—His—Leu—Methylester are particularly preferred.

Antagonists of the invention are useful for treating diseases involving the malignant or benign proliferation of tissue, such as all forms of cancer where bombesin-related, GRP-related, or GRF-related substances act as autocrine or paracrine mitotic factors, e.g., cancers of the gastrointestinal tract, pancreatic cancer, colon cancer, lung cancer, particularly the small cell subtype, prostate or breast cancer; or for treating artherosclerosis, and disorders of gastrointestinal tissues related to gastric and pancreatic secretions and motility; for example, for causing the suppression of amylase secretion, or for appetite control. GRF antagonists suppress the release of growth hormone and, therefore, may be used to slow down the progression of muscular dystrophy or for treating diabetes, or diabetes-related retinopathy.

In the generic formulas given above, when $R_1$, $R_2$, $R_4$ of I, $R_5$ of I, $R_6$ of I, $R_{22}$ of I, $R_3$ of II, $R_5$ of II, $R_6$ of II, $R_7$ of II, $Z_2$ of III, $Z_3$ III, $Z_4$ of III, $Z_{20}$ of IV, or $Z_{30}$ of IV is an aromatic, lipophilic group, the in vivo activity can be long lasting, and delivery of the compounds of the invention to the target tissue can be facilitated.

The identifying group of an α-amino acid is the atom or group of atoms, other than the α-carbonyl carbon atom, the α-amino nitrogen atom, or the H atom, bound to the asymmetric α-carbon atom. To illustrate by examples, the identifying group of alanine is $CH_3$, the identifying group of valine is $(CH_3)_2CH$, the identifying group of lysine is $H_3N^+(CH_2)_4$ and the identifying group of phenylalanine is $(C_6H_6)CH_2$. The identifying group of a β- or γ-amino acid is the analagous atom or group of atoms bound to respectively, the β- or the γ-carbon atom. Where the identifying group of an amino acid is not specified it may be α, β, or γ.

Other features and advantages of the invention will be apparent from the following description of the preferred embodiments thereof, and from the claims.

DESCRIPTION OF THE PREFERRED EMBODIMENTS

We first briefly describe the drawings.

Drawings

Figure 1:
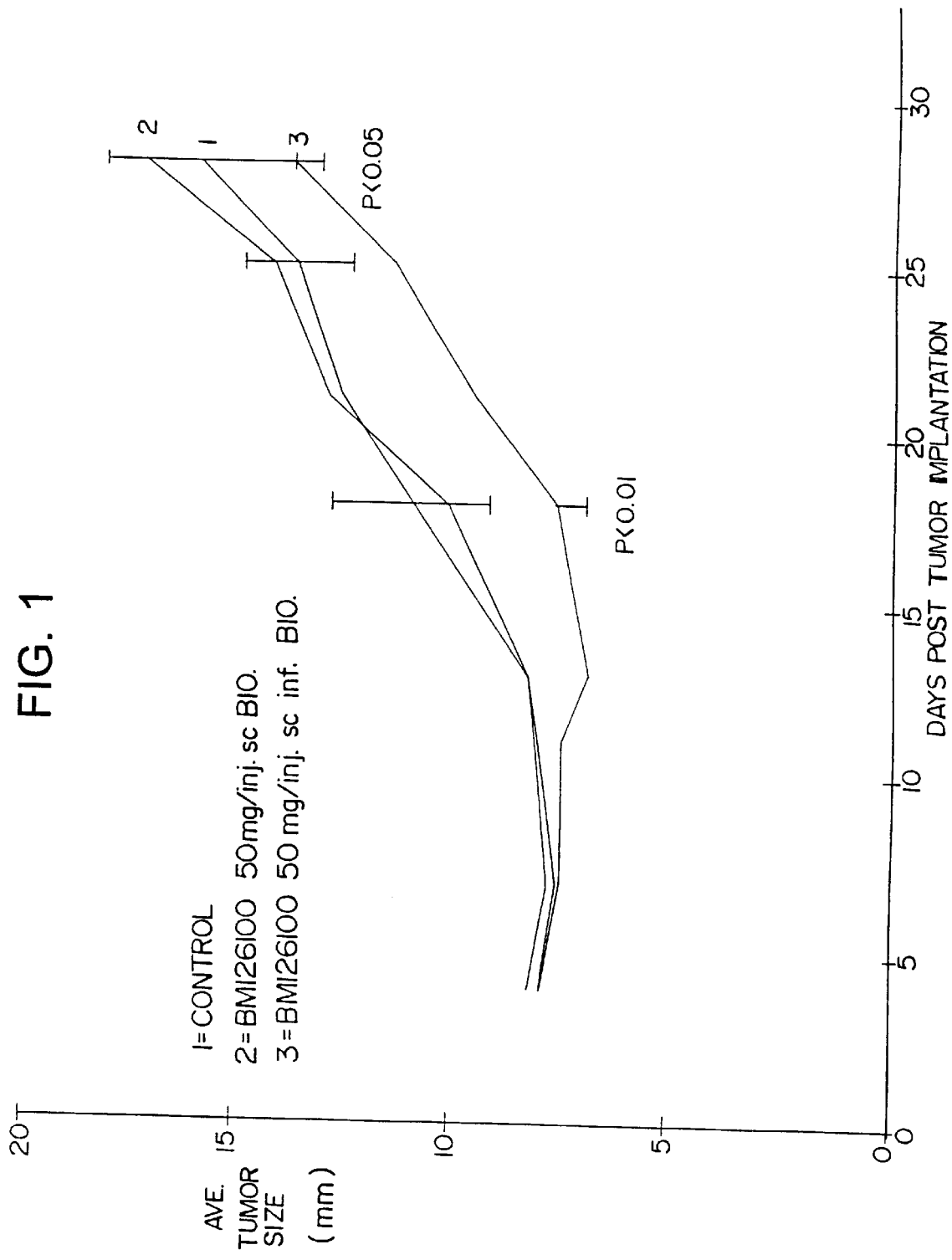
FIG. 1 is a graph of tumor growth curves for the small cell lung cancer (NCI-H69) xenografts.

We now describe the structure, synthesis, and use of the preferred embodiments of the invention.

Structure

Peptides of the invention have either a non-peptide bond in at least one of the indicated positions, or a statine, β-amino acid, or γ-amino acid substitution, e.g., $sta^8$-des- Met⁹ litorin. By non-peptide bond is meant e.g., that the carbon atom participating in the bond between two residues is reduced from a carbonyl carbon to a methylene carbon. The peptide bond reduction method which yields this non-peptide bond is described in Coy et al., U.S. patent application Ser. No. 879,348 now U.S. Pat. No. 4,803,261, assigned to the same assignee as the present application, hereby incorporated by reference. Any one of the amino acids in positions 0, 1, 2, and 9 of the litorin antagonists may be deleted from the peptides, and the peptides are still active as antagonists.

The peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis of Litorin, Bombesin, and GRF Analogs

The synthesis of the bombesin antagonist pGlu—Gln—Trp—Ala—Val—Gly—His—LeuΨ[CH$_2$NH]Leu—NH$_2$, (SEQ ID NO: 7) follows. Other bombesin, GRP, or GRF antagonists can be prepared by making appropriate modifications of the following synthetic methods.

The first step is the preparation of the intermediate
p G l u — G l n — T r p — A l a — V a l — G l y — H i s (benzyloxycarbonyl)—LeuΨ[CH$_2$NH]Leu-benzhydrylamine resin, as follows.

Benzhydrylamine-polystyrene resin (Vega Biochemicals, Inc.) (0.97 g, 0.5 mmole) in the chloride ion form is placed in the reaction vessel of a Beckman 990B 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin is stirred with alpha-t-butoxycarbonyl(Boc)-leucine and diisopropylcarbodiimide (1.5 mmole each) in methylene chloride for 1 hour, and the resulting amino acid resin is then cycled through steps (a) to (f) in the above wash program. Boc-leucine aldehyde (1.25 mmoles), prepared by the method of Fehrentz and Castro, Synthesis, p. 676 (1983), is dissolved in 5 ml of dry dimethylformamide (DMF) and added to the resin TFA salt suspension followed by the addition of 100 mg (2 mmoles) of sodium cyanoborohydride (Sasaki and Coy, Peptides 8:119–121 (1987); Coy et al., id.). After stirring for 1 hour, the resin mixture is found to be negative to ninhydrin reaction (1 min.), indicating complete derivatization of the free amino group.

The following amino acids (1.5 mmole) are then coupled successively in the presence diisopropylcarbodiimide (1.5 mmole), and the resulting amino acid resin is cycled through washing/deblocking steps (a) to (f) in the same procedure as above: Boc—His(benzyloxycarbonyl), Boc-Gly (coupled as a 6M excess of the p—nitrophenylester), Boc-Val, Boc-Ala, Boc-Trp, Boc-Gln (coupled as a 6M excess of the p—nitrophenylester), and pGlu. The completed resin is then washed with methanol and air dried.

The resin described above (1.6 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen, and free peptide is precipitated and washed with ether. The crude peptide is dissolved in a minimum volume of 2M acetic acid and eluted on a column (2.5×100 mm) of SEPHADEX G-25 (Pharmacia Fine Chemicals, Inc.). Fractions containing a major component by uv absorption and thin layer chromatography (TLC) are then pooled, evaporated to a small volume and applied to a column (2.5×50 cm) of octadecylsilane-silica (WHATMAN LRP-1, 15–20 μm mesh size).

The peptide is eluted with a linear gradient of 0–30% acetonitrile in 0.1% trifluoroacetic acid in water. Fractions are examined by TLC and analytical high performance liquid chromatography (HPLC) and pooled to give maximum purity. Repeated lyophilization of the solution from water gives 60 mg of the product as a white, fluffy powder.

The product is found to be homogeneous by HPLC and TLC. Amino acid analysis of an acid hydrolysate confirms the composition of the peptide. The presence of the LeuΨ [CH$_2$—NH]Leu bond is demonstrated by fast atom bombardment mass spectrometry. pGlu—Gln—Trp—Ala—Val—Gly—His—PheΨ[CH$_2$NH]Leu—NH$_2$ (SEQ ID NO: 6) and pGlu—Gln—Trp—Ala—Val—Gly—His—LeuΨ [CH$_2$NH]Leu—NH$_2$ or (SEQ ID NO: 7) other peptides are prepared in similar yields in an analogous fashion by appropriately modifying the above procedure.

Solid phase synthesis of D-Phe¹, Leu⁸Ψ[CH$_2$NH]D-Phe⁹-litorin, D-Phe—Gln—Trp—Ala—Val—Gly—His—LeuΨ [CH$_2$NH]—D-Phe—NH$_2$, was carried out as follows:

Boc-D-Phe—Gln—Trp—Ala—Val—Gly—His(tosyl)—LeuΨ[CH$_2$NH]—D-Phe—benzhydrylamine resin was synthesized first.

Benzhydrylamine-polystyrene resin (Advanced ChemTech, Inc.) (1.25 g, 0.5 mmole) in the chloride ion form is placed in the reaction vessel of an advanced CHEMTECH ACT 200 peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-D-phenylalanine and diisopropylcarbodiimide (1.5 mmole each) in methylene chloride for 1 h and the resulting amino acid resin is then cycled through steps (a) to (g) in the above wash program. The Boc group is then removed by TFA treatment. Boc-leucine aldehyde (1.25 mmoles), prepared by the method of Fehrentz and Castro (1), is dissolved in 5 ml of dry DMF and added to the resin TFA salt suspension followed by the addition of 100 mg (2 mmoles) of sodium cyanoborohydride (2,3). After stirring for 1 h, the resin mixure is found to be negative to ninhydrin reaction (1 min) indicating complete derivatization of the free amino group.

The following amino acids (1.5 mmole) are then coupled successively by the same procedure:
Boc-His(benzyloxycarbonyl), Boc-Gly, Boc-Val, Boc-Ala, Boc-Trp, Boc-Gln (coupled in the presence of 1 equiv. hydroxybenzotriazole), Boc-D-Phe (coupled in the presence of 1 equiv. hydroxybenzotriazole). After drying, the peptide resin weighed 1.93 g.

The resin (1.93 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen and free peptide precipitated and washed with ether. The crude peptide is dissolved in a minimum volume of 2M acetic acid and eluted on a column (2.5×100 mm) of SEPHADEX G-25. Fractions containing a major component by UV absorption and thin layer chromatography are then pooled, evaporated to a small volume and applied to a column (2.5×50 cm) of VYDAC octadecylsilane (10–15 uM). This is eluted with a linear gradient of 15–45% acetonitrile in 0.1% trifluoroacetic acid in water. Fractions are examined by thin layer chromatography and analytical high performance liquid chromatography and pooled to give maximum purity. Repeated lyophlization of the solution from water gives 120 mg of the product as a white, fluffy powder.

The product is found to be homogeneous by hplc and tlc. Amino acid analysis of an acid hydrolysate confirms the composition of the octapeptide. The presence of the Leu$\Psi$ [$CH_2NH$] peptide bond is demonstrated by fast atom bombardment mass spectrometry.

Solid phase synthesis of D-Phe$^1$—Leu$^8$des—Met$^9$ litorin, D-Phe—Gln—Trp—Ala—Val—Gly—His—Leu—$NH_2$, was carried out as follows.

Step (1): Benzhydrylamine-polystyrene resin (Advanced ChemTech, Inc. (0.62 gm, 0.25 mmole) in the chloride ion form is placed in the reacton vessel of an ACT 200 peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-leucine and diisopropylcarbodiimide (1.5 mmole each) in methylene chloride for 1 hr and the resulting amino acid resin is then cycled through steps (a) to (g) in the above wash program. The following amino acids (1.5 mmole) are then coupled successively by the same procedure: Boc-His (benzyloxycarbonyl), Boc-Gly, Boc-Val, Boc-Ala, Boc-Trp, Boc-Gln (coupled as a 6M excess of the p-nitrophenylester, and pGlu (coupled in the presence of hydroxzybenzotriazole). After drying, the peptide resin weighed 0.92 g.

Step (2): The resin (0.92 g) is then mixed with anisole (5 ml), dithiothreitol (200 mg) and anhydrous hydrogen fluoride (35 ml) at 0° C. and stirred for 45 min. Excess hydrogen fluoride is evaporated rapidly under a stream of dry nitrogen and free peptide precipitated and washed with ether. The crude peptide is dissolved in a minimum volume of 2M acetic acid and eluted on a column (2.5×100 cm) of SEPHADEX G-25. Fractions containing a major component by UV absorption and thin layer chromatography are then pooled, evaporated to a small volume and applied to a column (2.5×50 cm) of VYDAC octadecylsilane (10–15 microM). The column is eluted with a linear gradient of 0–30% acetonitrile in 0.1% trifluoroacetic acid in water. Fractions are examined by thin layer chromatography and pooled to give maximum purity. Repeated lyophilization of the solution from water gives a white, fluffy powder; this product is found to be homogeneous by HPLC and TLC. Amino acid analysis of an acid hydrolysate confirms the composition of the peptide.

Synthesis of D-Nal—Gln—Trp—Ala—Val—Gly—His—Leu—$NH_2$ was accomplished using the same procedure as described above (0.62 g, 0.25 mmole of benzyhydrylamine resin in step (1), and 0.92 g in step (2)).

Synthesis of N-acetyl-D-Phe—Gln—Trp—Ala—Val—Gly—His—Leu—$NH_2$ was accomplished using the same procedure as that described above, using 0.62 g (0.25 mmole) of benzhydrylamine resin in step (1), and mixing 0.92 g of the resin with anisole in step(2), except that the final Boc group was removed and the resin acetylated with acetic anhydride in methylene chloride.

Synthesis of D-Phe—Gln—Trp—Ala—Val—N—Me—D—Ala—His(Tos)—Leu—O-resin is as follows:

Boc-Leu—O-MERRIFIELD resin (1.0 g. 0.5 mmole) is placed in the reaction vessel of an ADVANCED CHEMTECH ACT 200 automatic peptide synthesizer programmed to perform the following reaction/wash cycle: (a) methylene chloride; (b) 33% trifluoroacetic acid in methylene chloride (2 times for 1 and 25 min. each); (c) propanol; (d) dimethylformamide; (e) 10% triethylamine in dimethylformamide; (f) dimethylformamide.

The neutralized resin is stirred with Boc-$N^{im}$-tosy-histidine and diisopropylcarbodiimide (1.5 mmole each) in methylene chloride for 1 h. and the resulting amino acid resin is then cycled through steps (a) to (f) in the above wash program. The Boc group is then removed by TFA treatment. The following amino acids (1.5 mmole) are then coupled successively by the same procedure: Boc-N-Me-D-Ala (purchased from Bachem, Inc., CA), Boc-Val, Boc-Ala, Boc-Trp, Boc-Gln (coupled in the presence of 1 equiv. hydroxybenzotriazole), and Boc-D-Phe. After the last coupling was complete, the final Boc group was removed by TFA treatment as already described. After drying, the peptide resin weighed 1.28 g.

Synthesis of D-$F_5$—Phe—Gln—Trp—Ala—Val—D—Ala—His(Tos)—Leu—O-resin is as follows:

This analogue is prepared under the same conditions described above, except that Boc-D-Ala is used in place of N-Me-D-Ala and Boc-D-$F_5$Phe in place of D-Phe.

Synthesis of D-$F_5$Phe—Gln—Trp—Ala—Val—D—Ala—His—Leu-methyl ester is as follows.

This peptide is cleaved from the MERRIFIELD resin described above under the same conditions, to give 198 mg of the product as a white, fluffy powder.

The product is found to be homogeneous by HPLC and tlc. Amino acid analysis of an acid hydrolysate confirms the composition of the octapeptide and fast atom bombardment mass spectrometry gives the expected molecular weight for the peptide.

Synthesis of D-Phe—Gln—Trp—Ala—Val—N—Me—D—Ala—His—Leu-methyl ester is as follows:

The MERRIFIELD resin described above (1.28 g, 0.5 mmole) is suspended in methanol containing 10% triethylamine and stirred at room temperature for 3 days. After filtration, the solution is evaporated to an oil which is dissolved in water and eluted on a column of VYDAC octadecylsilane (10–15 $\mu$M) with a linear gradient of 10–40% acetonitrile in 0.1% trifluoroacetic acid in water. Fractions are examined by thin layer chromatography and analytical high performance liquid chromatography and pooled to give maximum purity. Repeated lyophilization of the solution from water gives 49 mg of the product as a white, fluffy powder.

The product is found to be homogeneous by HPLC and TLC. Amino acid analysis of an acid hydrolysate confirms the composition of the octapeptide and fast atom bombardment mass spectrometry gives the expected molecular weight for the peptide.

The synthesis of Sta$^8$-des-Met$^9$ litorin follows. A statine, AHPPA, or ACHPA residue can be substituted in place of any two amino acids of the peptide, where the peptide contains only peptide bonds. For example, sta$^8$-des Met$^9$ litorin was prepared in an analagous fashion by first coupling statine to the resin and then proceeding with the addition of Boc-His(benzylocarbonyl). Statine or Boc-statine can be synthesized according to the method of Rich et al., 1978, J. Organic Chem. 43; 3624; and Rich et al., 1980, J. Med. Chem. 23: 27, and AHPPA and ACHPA can be synthesized according to the method of Hui et al., 1987, J. Med. Chem. 30: 1287; Schuda et al., 1988, J. Org. Chem. 53:873; and Rich et al., 1988, J. Org. Chem. 53:869.

Solid-phase synthesis of the peptide BIM-26120, pGlu—Gln—Trp—Ala—Val—Gly—His—Sta—$NH_2$ (SEQ ID NO: 4), was accomplished through the use of the following procedures in which alpha-t-butoxycarbonyl statine (prepared by the procedure of Rich et al., J. Org. Chem. 1978, 43, 3624) is first coupled to methylbenzhydrylamine-polystyrene resin. After acetylation, the intermediate p-Glu—Trp—Ala—Val—Gly—His(benzyloxycarbonyl)—Sta-methylbenzhydrylamine resin (a precursor of SEQ ID NO: 4) is prepared. The synthetic procedure used for this preparation follows in detail:

1. Incorporation of alpha-t-butoxycarbonyl statine on methylbenzhydrylamine resin.

Methylbenzhydrylamine-polystyrene resin (Vega Biochemicals, Inc.) (1.0 g, 0.73 mmol) in the chloride ion form is placed in the reaction vessel of a VEGA 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin is mixed for 18 hours with the preformed active ester made from alpha-t-butoxycarbonyl statine (1.46 mmol), diisopropyl carbodiimide (2 mmol), and hydroxybenzotriazole hydrate (1.46 mmol in dimethylformamide at 0° C. for one hour. The resulting amino acid resin is washed on the synthesizer with dimethylformamide and then methylene chloride. The resin mixture at this point was found by the Kaiser ninhydrin test (5 minutes) to have an 84% level of statine incorporation on the resin.

Acetylation was performed by mixing the amino-acid resin for 15 minutes with N-acetyl imidazole (5 mmol) in methylene chloride. Derivatization to the 94–99% level of the free amino groups of the resin was indicated by the Kaiser ninhydrin test (5 minutes). The Boc-statine-resin is then washed with methylene chloride.

2. Couplings of the Remaining Amino Acids.

The peptide synthesizer is programmed to perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (2.19 mmol) are then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin is washed on the synthesizer with dimethylformamide and then methylene chloride, and then cycled through the washing and deblocking steps (a) to (f) in the procedure described above.

Boc-His (benzyloxycarbonyl) (coupled in the presence of 2 equivalents hydroxybenzotriazole); Boc-Gly; Boc-Val; Boc-Ala and Boc-Trp (coupled as the preformed hydroxybenzotriazole active esters made by reaction at 0° C. for one hour with 1 equivalent hydroxybenzotriazole hydrate); Boc-Gln and pGlu (also coupled as the preformed active esters of hydroxybenzotriazole made by reaction at 0° C. for one hour with 1 equivalent hydroxybenzotriazole hydrate). The completed peptide-resin is then washed with methanol and air dried.

The peptide-resin described above (1.60 g, 0.73 mmol) is mixed with anisole (2.5 mL), dithioerythreitol (50 mg), and anhydrous hydrogen fluoride (30 mL) at 0° C. for one hour. Excess hydrogen fluoride is evaporated rapidly under a stream of dry nitrogen, and the free peptide is precipitated and washed with ether. The crude peptide is dissolved in 100 mL of 1M acetic acid and the solution is then evaporated under reduced pressure. The crude peptide is dissolved in a minimum volume of methanol/water 1/1 and triturated with 10 volumes of ethyl acetate.

The triturated peptide is applied to a column (9.4 mm I.D.×50 cm) of octadecylsilane-silica (WHATMAN DAR-TISIL 10 ODS-2 M 9). The peptide is eluted with a linear gradient of 20–80% of 20/80 0.1% trifluoroacetic acid/acetonitrile in 0.1% trifluoroacetic acid in water. Fractions are examined by TLC and analytical high performance liquid chromatography (HPLC) and pooled to give maximum purity. Lyophilization of the solution from water gives 77 mg of the product as a white fluffy powder.

Other compounds including D-Cps$^1$, β-leu$^8$, desMet$^9$ Litorin can be prepared as above and tested for effectiveness as agonists or antagonists in the test program described below.

GRF analogues were prepared by solid-phase synthesis on methylbenzhydrylamine resin. The parent GRF(1–29) peptidyl-resin was assembled on 4-methylbenzhydrylamine functionalized, 1% crosslinked polystyrene resin (0.41 mequiv. g$^{-1}$), on 2 mmol scale utilizing an ADVANCED CHEMTECH ACT 200 synthesizer, using the following protocol: deblocking, 33% TFA (1 min, 25 min); DCM wash cycle; PrOH wash cycle; neutralization, 10% DIEA (2 wash cycles); DMF wash cycle; coupling of preformed HOBt esters (formed during deprotection), 45 min in DMF, 15 min DMAP; PrOH wash cycle; DCM wash cycle. Coupling reactions were monitored qualitatively with the ninhydrin test (Kaiser et al, Anal. Biochem. 1970, 34, 595). The peptidylresin was divided into aliquots and the various analogues then assembled on a 0.25 mmol scale. The reduced peptide bonds were formed by the reductive alkylation of the deprotected N$^\alpha$-amino group with the appropriate protected amino acid aldehyde (3.0 equiv.) in the presence of NaBH$_3$CN (10 equiv.) in DMF (25 mL) containing 1% acetic acid at ambient temperature for 16 h.

The introduction of the reduced peptide bond was accomplished by the reductive alkylation of the resin-bound peptide amino terminus with a preformed protected amino acid aldehyde (Sasaki et al., Peptides 1987, 8, 119; Sasaki et al, J. Med. Chem. 1987, 30, 1162). The protected amino acid aldehydes were prepared in two steps using a modification of the method of Fehrentz and Castro: (Fehrentz, Synthesis, 1983, 676) the protected amino acids were converted to the corresponding N,O-dimethylhydroxamates by reaction with an excess of N,O-dimethylhydroxylamine hydrochloride (1.1 equiv.) and dicyclohexylcarbodiimide (1.1 equiv.) in dichloromethane containing an excess of diisopropylethylamine (4 equiv.) at 0° C. The reaction was allowed to warm up to ambient temperature over 16 h with stirring. The crude N,O-dimethylhydroxamates were isolated as oils after washing with 3M HCl (3×30 mL), 3M NaOH (3×30 mL), water (3×30 mL), drying over MgSO$_4$ and evaporation to dryness at reduced pressure. The N,O-hydroxamates were then reduced with LiAlH$_4$ in tetrahydrofuran at 0° C. The reaction was followed by TLC and the crude aldehydes isolated as oils which were briefly stored at −20° C. until used. The isosteres were formed by the reductive alkylation of the preformed protected amino-acid aldehyde (3 equiv.) with an excess of NaBH$_3$CN in acidified DMF. The progress of the alkylation was monitored with the qualitative ninhydrin test and most reactions produced a pink or red colour which was taken as the end point. The method was shown to be free of racemization in a model study (Coy et al, Tetrahedron 1988, 3, 835). However, appreciable racemization can occur if the aldehyde is stored for a prolonged period before use. Peptide assembly was completed using the same protocol as before. No attempt was made to block any remaining primary amino groups or to protect the secondary amino group formed during the alkylation, since previous work has shown this moiety to be unreactive during subsequent coupling reactions (Sasaki, Peptides, supra; Hocart et al., J. Med. Chem. 1988, 31, 1820. The peptides were cleaved from the resin support with simultaneous side-chain acidolysis using anhydrous hydrogen fluoride containing anisole (~30% v/v) and dithiothreitol (~0.6% w/v) as scavengers for 1 h at 0° C.

The peptides were then purified by gel filtration and RP-HPLC to a final purity of >92.5% as judged by analytical RP-HPLC. The crude peptides were subjected initially to gel permeation chromatography on SEPHADEX G50 (2.5×100 cm) with 2M acetic acid eluent. Final purification was effected by preparative RP-HPLC on $C_{18}$ bonded silica gel (VYDAC $C_{18}$, 10–15 μm, 1.0×45 cm) eluted with a linear acetonitrile gradient with a constant concentration of trifluoroacetic acid (0.1% v/v). The linear gradient was generated using a CHROMAT-A-TROL MODEL II (Eldex Laboratories Inc.) gradient maker. The separations were monitored at 280 nm, by TLC on silica gel plates (MERCK F60) and analytical RP-HPLC. The fractions containing the product were pooled, concentrated in vacuo and subjected to filtration. Each peptide was obtained as a fluffy white powder of constant weight by lyophilisation from aqueous acetic acid. The purity of the final peptides was assessed by RP-HPLC. Analytical RP-HPCL's were recorded using a VYDAC $C_{18}$ support (4.6×250 mm, 5 μm, 300 angstrom pore size, Liquid Separations Group). A linear gradient from 30% to 60% acetonitrile over 30 min with a constant concentration of trifluoroacetic acid (0.1% v/v) was employed for all the analyses at a flow rate of 1.5 mL min$^{-1}$. Column eluent was monitored at 215 nm. The retention time and purity of each peptide was assessed by the Rainin Dynamax HPLC Method Manager.

Amino acid analyses of the peptides was done by hydrolysis in vacuo (110° C.; 20 h) in 4M methanesulphonic acid containing 0.2% 3-(2-aminoethyl)-indole[2,23] (Pierce). Amino acid analyses were performed on the hydrolysates using an LKB 4150 analyser, equipped with an ULTROPAC 11 column (6×273 mm) and a SHIMADZU C-R3A recording integrator with in-house software. The buffer sequence pH 3.20 (17.5 min), pH 4.25 (32 min), pH 10.00 (borate; 16 min) and temperature sequence 50° C. (5 min), 55° C. (5 min), 58° C. (39.5 min), 65° C. (7 min), 80° C. (17 min) were used. Standard retention times were as follows: His, 65.1; Lys, 70.1; $NH_3$, 74.3; Arg, 77.2 min respectively. The results are shown in Table 5.

FAB-MS was conducted by Oneida Research Services, Inc., Whitesboro, N.Y. using a FINNIGAN TSQ-70 equipped with an ION TECH FAB gun at 6 kV with a primary current of 0.2 mA whilst scanning from 2800 to 3500 amu. The samples were dissolved in a "Magic Bullet" matrix and the results are given in Table 4. The position of the pseudopeptide bond in each of the synthesized peptides is shown in Table 6.

Solid phase synthesis of Ser$^9$Ψ[CH$_2$NH]Tyr$^{10}$GRF (1–29), Tyr—Ala—Asp—Ala—Ile—Phe—Thr—Asn—SerΨ[CH$_2$NH]Tyr—Arg—Lys—Val—Leu—Gly—Gln—Leu—Ser—Ala—Arg—Lys—Leu—Leu—Gln—Asp—Ile—Met—Ser—Arg—NH$_2$ (SEQ ID NO: 5), was carried out as follows.

Methylbenzhydrylamine resin (Advanced ChemTech, Inc.) (0.62 g, 0.25 mmole) in the chloride ion form is placed in the reaction vessel of an ADVANCED CHEMTECH ACT 200 peptide synthesizer programmed to perform the following reaction cycle: (a) 33% trifluoroacetic acid in methylene chloride (2 times for 1 and 25 min each); (b) DCM wash; (c) PrOH wash; (d) neutralization; (e) 10% diisopropyl ethylamine (DIEA) in chloroform (2 washes); (f) 0.75 mM DMF wash; (g) coupling of preformed activated amino acid (HOBT) esters, 45 min. in DMF; (h) 15 min. DMAP; (i) PrOH wash; (j) DCM wash. The pseudopeptide bond was incorporated by racemization-free reductive alkylation with a preformed protected amino-acid aldehyde in the presence of NaCNBH$_3$ in acidified DMF, as described by Coy et al., 1988, Tetrahedron 44:835 and Hocart et al., 1988, J. Med. Chem. 31:1820.

The resin bound peptide was elongated by repeating cycles (a–j) to give Boc-Tyr—Arg—Lys—Ala—Leu—Gly—Gln—Leu—Ser—Ala—Arg—Lys—Leu—Leu—Gln—Asp—Ile—Met—Ser—Arg—Gln—Gln—Gly—Glu—Ser—Asn—Gln—Glu—Arg—Gly—Ala—Arg—Ala—Arg—Leu—methylbenzhydrylamine. (SEQ ID NO: 10). The Boc group is then removed by TFA treatment. Boc-serine aldehyde (0.75 mmoles), prepared by the method of Fehrentz and Castro (1), is dissolved in 5 ml of dry DMF and added to the resin TFA salt suspension followed by the addition of 100 mg (2 mmoles) of sodium cyanoborohydride (2,3). After stirring for 1 h, the resin mixture is found to be negative to ninhydrin reaction (1 min) indicating complete derivatization of the free amino group.

The following amino acids (1.5 mmole) are then coupled successively by the same procedure: Boc-Asn, Boc-Thr (benzyl), Boc-Phe, Boc-Ile, Boc-Ala, Boc-Asp (o-cyclohexyl ester), Boc-Ala, Boc-Tyr (dichlorobenzyl). After drying, the peptide resin weighed 1 g.

The aldehydes were prepared by reduction of the protected dimethylhydroxamates with LiAlH$_4$ (0.75 equiv.) for 180 min. at 0° C. The resin (1.0 g, 0.25 mmole) is mixed with anisole (5 ml), anhydrous hydrogen fluoride (35 ml), and 100 mg dithiothretol at 0° C. and stirred for 45 min. Excess hydrogen fluoride is evaporated rapidly under a stream of dry nitrogen and free peptide precipitated and washed with ether. The crude peptide is dissolved in a minimum volume of 2M acetic acid and eluted on a column (2.5×100 mm) of SEPHADEX G-50. Fractions containing a major component by UV absorption and thin layer chromatography are then pooled, evaporated to a small volume and applied to a column (2.5×50 cm) of VYDAC octadecylsilane (10–15 uM). This is eluted with a linear gradient of 0–50% acetonitrile in 0.1% trifluoroacetic acid in water. Fractions are examined by thin layer chromatography and analytical high performance liquid chromatography and pooled to give maximum purity. Repeated lyophilization of the solution from water gives 8.0 mg of the product as a white, fluffy powder.

The product is found to be homogeneous by HPLC and TLC. Amino acid analysis of an acid hydrolysate confirms the composition of the octapeptide. The presence of the SerΨ[CH$_2$NH]Tyr psuedo peptide bond is demonstrated by fast atom bombardment mass spectrometry.

A statine, AHPPA, ACHPA, β-amino acid, or γ-amino acid residue is added in the same way as is a natural α-amino acid residue, by coupling as a Boc derivative.

All but one of the peptides shown in Table 4 gave satisfactory amino acid analyses and the expected FAB-MS value within the error of the methods (see Table 4 and Table 5). The analogue [Asn$^8$Ψ[CH$_2$NH]—Ser$^9$]GRF(1–29)NH$_2$ could not be synthesised. The reaction of Boc-Asn(Xan) CHO with Ser(Bzl)-[resin] was very slow and no appreciable reaction was noted after several prolonged alkylations. This lack of reactivity may be due to the steric hindrance of the bulky side-chain protecting groups since, in a series of Substance P analogues, Boc—Gln(Xan)CHO was used successfully (Qain et al., J. Biol. Chem. 1989, 16667). No problems were experienced with the preparation or used of Boc—Asp(OCHx)CHO and no evidence of over reduction to homo-Ser was observed.

Phase 1
3T3 Peptide Stimulated [$^3$H] Thymidine Uptake Assay
Cell Culture.

Stock cultures of Swiss 3T3 cells are grown in DULBECCO'S MODIFIED EAGLES MEDIUM (DMEM) supplemented with 10% fetal calf serum in humidified atmosphere of 10% $CO_2$/90% air at 37° C. For experimental use, the cells are seeded into 24-well cluster trays and used four days after the last change of medium. The cells are arrested in the G1/G0 phase of the cell cycle by changing to serum-free DMEM 24 hours prior to the thymidine uptake assay.

Assay of DNA Synthesis.

The cells are washed twice with 1 ml aliquots of DMEM (-serum) then incubated with DMEM (-serum), 0.5 μm [methyl-$^3$H] thymidine (20 Ci/mmole, New England Nuclear), bombesin (3 nM), and initially four concentrations of the test compounds (1, 10, 100, 1000 nM) in a final volume of 1.0 ml. After 28 hours at 37° C., [methyl-$^3$H] thymidine incorporation into acid-insoluble pools is assayed as follows. The cells are washed twice with ice-cold 0.9% NaCl (1 ml aliquots), and acid soluble radioactivity is removed by a 30 min. (4° C.) incubation with 5% trichloroacetic acid (TCA). The cultures are then washed once (1 ml) with 95% ethanol and solubilized by a 30 min. incubation (1 ml) with 0.1N NaOH. The solubilized material is transferred to vials containing 10 ml SCINTA (Packard), and the radioactivity is determined by liquid scintillation spectrometry.

Phase 2
Small Cell Carcinoma (SCLC)—Bombesin Stimulated [$^3$H] Thymidine Uptake Assay
Cell Culture.

Cultures of the human cell carcinoma cell line (NCI-H69) (obtained from the American Type Culture Association) are maintained in RPMI 1640 medium supplemented with 10% fetal calf serum in 10% $CO_2$/90% air at 37° C. Twenty-four hours prior to assay, the cells are washed with serum-free medium and seeded in 24-well cluster trays.

Assay of DNA Synthesis.

Bombesin (1 nM), 0.5 μM [methyl-3H] thymidine (20 Ci/mmole, New England Nuclear), and four concentrations of the test compounds (1, 10, 100, 1000 nM) are added to the cultures to achieve a final volume of 0.5 ml. After a 28 hr incubation at 37° C., the cells are collected onto GF/B glass fiber filters, and the DNA is precipitated with ice-cold TCA. [$^3$H] thymidine incorporation into acid-insoluble fractions of DNA is determined by liquid scintillation spectrometry.

Phase 3
Peptide-Induced Pancreatitis

Male, Sprague-Dawley rats (250 g) are used for these experiments. The test compound, or 0.9% NaCl is administered s.c. 15 min. prior to the bombesin injection. Bombesin injections are given s.c. at a dose of 10 μg/kg, and blood samples are obtained at 1 hr.30 min., 3 hr. and 6 hr. Plasma amylase concentration are determined by the Pantrak Amylase test.

Phase 4
In Vitro Inhibition of [$^{125}$I] Gastrin Releasing Peptide (GRP) Binding to Bombesin Receptors Membranes from various tissues (rat brain, rat pancreas, rat anterior pituitary, SCLC, 3T3 cells) are prepared by homogenization in 50 mM TRISHCl containing 0.1% bovine serum albumin and 0.1 mg/ml bacitracin followed by two centrifugations (39,000×g×15 min., 4° C.) with an intermediate resuspension in fresh buffer. For assay, aliquots (0.8 ml) are incubated with 0.5 nM [$^{125}$I]GRP (~2000 Ci/mmol, Amersham Corp.) and various concentrations of the test compounds in a final volume of 0.5 ml. After a 30 minute incubation at 4° C., the binding reaction is terminated by rapid filtration through WHATMAN GF/C filters that have been pre-soaked in 0.3% aqueous polethyleneimine to reduce the level of nonspecific binding. The filters and tubes are washed three times with 4 ml aliquots of ice-cold buffer, and the radioactivity trapped on the filters is counted by gamma-spectrometry. Specific binding is defined as the total. [$^{125}$I]GRP bound minus that bound in the presence of 1000 nM bombesin or a related peptide.

Phase 5
Inhibition of Gastrin Release

The stomachs of anesthetized rats are perfused with saline collected over 15 minute periods via pyloric cannulation while the test peptide is infused through the femoral vein for periods between 0 and 150 minutes.

Phase 6
In Vivo Antitumor Activity

NCI-H69 small cell lung carcinoma cells were transplanted from in vitro culture by implanting each animal with the equivalent of 5 confluent 75 $cm^2$ tissue culture flasks in the right flank. In vitro NCI-H69 cells grow as a suspension of cellular aggregates. Therefore, no attempt was made to disaggregate the cell agglomerates by physical or chemical means. Tumor size was calculated as the average of two diameters, i.e., (length and width/2) mm.

Phase 7
Inhibition of Growth Hormone Release

Anterior pituitaries from adult male rats, weighing 200–250 g and housed under controlled conditions (lights on from 0500–1900 h), were dispersed using aseptic technique by a previously described trypsin/DNase method (Heiman et al., Endocrinology, 1985, 116, 410) derived from other methods (Hoefer et al., Mol. Cell. Endocrinol., 1984, 35, 229).

The dispersed cells were diluted with sterile-filtered DULBECCO'S MODIFIED EAGLES MEDIUM (MEM) (Gibco Laboratories, Grand Island, N.Y. (GIBCO)), which was supplemented with fetal calf serum (2.5%; GIBCO), horse serum (3%; GIBCO), fresh rat serum (10% stored on ice for no longer than 1 h) from the pituitary donors, MEM nonessential amino acids (1%; GIBCO), gentamycin (10/mg/mL; Sigma) and nystatin (10,000 U/mL; GIBCO). The cells were counted with a hemacytometer (approximately 2,000,000 cells per pituitary) and randomly plated at a density of 200,000 per well (Co-star cluster 24; Rochester Scientific Co., Rochester, N.Y.). The plated cells were maintained in the above Dulbecco's medium in a humidified atmosphere of 95% air and 5% $CO_2$ at 37° C. for 96 h.

In preparation for a hormone challenge, the cells were washed 3×with medium 199 (GIBCO) to remove old medium and floating cells. Each dose of secretagogue (diluted in siliconized test tubes) was tested in quadruplicate wells in medium 199 (total volume of 1 mL) containing BSA (1%; fraction V; Sigma Chemical Co., St. Louis, Mo.). Cells were pulsed in the presence of somatostatin (0.1 nM) to maintain control levels within narrow limits and to increase the ratio of maximally stimulated levels to basal secretory levels without adding additional growth factors or glucocorticoids. After 3 h at 37° C. in an air/carbon dioxide atmosphere (95/5%), the medium was removed and stored at −20° C. until assayed for hormone content.

Growth hormone (GH) in plasma and media was measured by a standard double antibody radioimmunoassay using components supplied by the NIDDK and the National Hormone and Pituitary Program, University of Maryland School of Medicine. Data are plotted as the mean values for a given dose of peptide obtained by pooling the means from individual experiments done in quadruplicate. The number of experiments for each analogue is given in Table 6. Potencies and 95% confidence intervals were calculateds by 4-point assay (Pugsley, Endocrinology, 1946, 39, 161).

Results of Assays of Test Peptides

A number of analogs of bombesin or GRP, each containing a non-peptide bond or a statine, AHPPA, or ACHPA, β-amino acid, or γ-amino acid residue, can be synthesized and tested in one or more of the above-described Phase 1–7 assays; the results of Phase 1 and 2 tests are given in Table 1 attached hereto. Table 1 shows formulas for the non-peptide analogues and results of in vitro inhibition of [$^{125}$I]GRP binding to 3T3 fibroblast bombesin receptors, and bombesin-stimulated [$^3$H]Thymidine uptake by cultured 3T3 cells. (3T3 GRP receptor and thymidine uptake data are expressed in IC50 (nM).) Table 1 also gives results for non-peptide bond-containing analogs of one other naturally-occurring peptide, Neuromedin C, whose C-terminal seven amino acids are similar to those of bombesin and GRP. (In Table 1, "Litorin" indicates a 9 residue peptide analog or its derivative, whereas "Neuromedin C" indicates a 10 residue analog or its derivative.)

In Table 1, the position of the non-peptide bond is indicated by the position of the symbol Ψ[CH$_2$NH]; i.e., Ψ[CH$_2$NH] is always shown preceding the amino acid which, in that peptide, is bonded to the amino acid N-terminal to it via the non-peptide bond. Where no amino acid is specified under "structure", the non-peptide bond links the two peptides represented by the numbers given as post-scripts.

In Table 1, it can be seen that a preferred placement of the non-peptide bond in litorin analogs is at the $A^8$–$A^9$ position; two of the most active analogs (as indicated by a low GRP receptor IC50 value) are BIM-26100 (Phe$^8$Ψ[CH$_2$NH]Leu$^9$) (SEQ ID NO: 6) and BIM-26101 (Leu$^8$Ψ[CH$_2$NH]Leu$^9$). (SEQ ID NO: 7)

In addition, as shown in Table 1, BIM-26113 (D—Phe$^1$, Leu$^8$Ψ[CH$_2$NH]Leu$^9$) and BIM-26114 (D—Nal$^1$, Leu$^8$Ψ[CH$_2$NH]Leu$^9$) are active in the 3T3 GRP receptor binding and thymidine uptake assays. Most notably, BIM-26136 (D—Nal$^1$, Leu$^8$Ψ[CH$_2$NH]Phe$^9$), which contains amino and carboxy terminal aromatic residues that are capable of forming a hydrophobic interaction, is the most potent analog. Finally, when statine or β-leucine replaces the $A^8$ and $A^9$ residues of litorin, the resultant analogs BIM-26120 and BIM-26182 are also potent antagonists.

Table 1 also shows that Neuromedin C analogs containing a non-peptide bond between residues $A^9$–$A^{10}$, e.g., BIM-26092, 26105, 26106, and 26107, are antagonists when tested in the 3T3 GRP receptor and thymidine uptake assays.

Table 1 also gives negative results for analogs of Neuromedin C and GRP 19–27, e.g., BIM-26108. Thus the non-peptide bond placement guidelines given herein should be used in conjunction with the routine assays described above to select useful antagonists.

Bombesin and Bombesin analogs have been shown to inhibit the effect of interleukin-2 (IL-2) (Fink et al., 1988, Klin. Wochenschr. 66, Suppl. 13, 273). Since IL-2 causes T lymphocytes to proliferate, it is possible that litorin antagonists may prevent the inhibitory effect of Bombesin or its analogs on IL-2. IL-2 stimulated lymphocytes are capable of effectively lysing small cell lung carcinoma cells in vitro. Although Bombesin antagonists have a direct antiproliferative effect on neoplastic tissues, they may also favor proliferation of lymphocytes having lytic activity for small cell lung carcinoma.

These observations prompted us to evaluate the effect of BIM-26100 on the in vivo growth of the SCLC tumor cell line described in Phase 6. Twenty athymic nude females, 5 to 6 weeks of age, were implanted on day 0 with the NCI-H69 human SCLC, individually identified and then randomized into the following vehicle control and test groups:

| Group No. | Treatment | No. Animals |
| --- | --- | --- |
| 1 | Saline vehicle treated control: 0.2 ml, s.c. inf., b.i.d., QD1-28 | 10 |
| 2 | BIM-26100: 50 μg/inj., s.c., b.i.d., QD1-28 | 5 |
| 3 | BIM-26100: 50 μg/inj., s.c. inf., b.i.d., QD1-28 | 5 |

(s.c. = subcutaneously;
inf. = infused around tumor;
inj. = injected;
b.i.d. = twice per day;
QD1-28 = daily treatment, on days 1–28.)

Growth of NCI-H69 xenografts and the tumor growth inhibitory activity of the bombesin antagonist BIM-26100 (pGlu—Gln—Trp—Ala—Val—Gly—His—PheΨ[CH$_2$NH]Leu—NH$_2$)(SEQ ID NO: 6) are illustrated as tumor growth curves in FIG. 1, and relative tumor sizes in Table 2. Administration of BIM-26100 as a s.c. infusion around the tumor significantly inhibited tumor growth. The effectiveness of the antitumor activity of BIM-26100 is evident in view of the large inoculum of NCI-H69 tumor cells (i.e., the equivalent of 5 confluent 75 cm$^2$ cell culture flasks per animal) and the agglomerated condition of the cells. In confluent flasks, NCI-H69 agglomerates are macroscopically visible and together resemble a metastatic tumor colony. Many such tumor colonies were implanted per animal. The dose of BIM-26100 was arbitrarily selected on the basis of compound availability and is not optimal. Higher doses of BIM-26100 may be administered, as indicated by body weight gain (minus tumor weight) gain during the course of treatment (Table 3). This suggest BIM-26100 completely lacks local or systemic toxicity and is useful therapeutically as an anti-growth factor with anti-tumor effects.

D-Phe—Gln—Trp—Ala—Val—N—methyl—D—Ala—His—Leu-methylester and D-F$_5$—Phe—Gln—Trp—Ala—Val—D—Ala—His—Leu-methylester were examined for their abilities to displace $^{125}$I-labeled bombesin from rat pancreatic acini cells and to inhibit amylase release from these cells produced by bombesin itself. The analogues exhibit potencies in the half-maximal effective dose ranges of 5–10 nM and are thus potent bombesin receptor antagonists.

Testing of GRF Analogs

Figure 2:
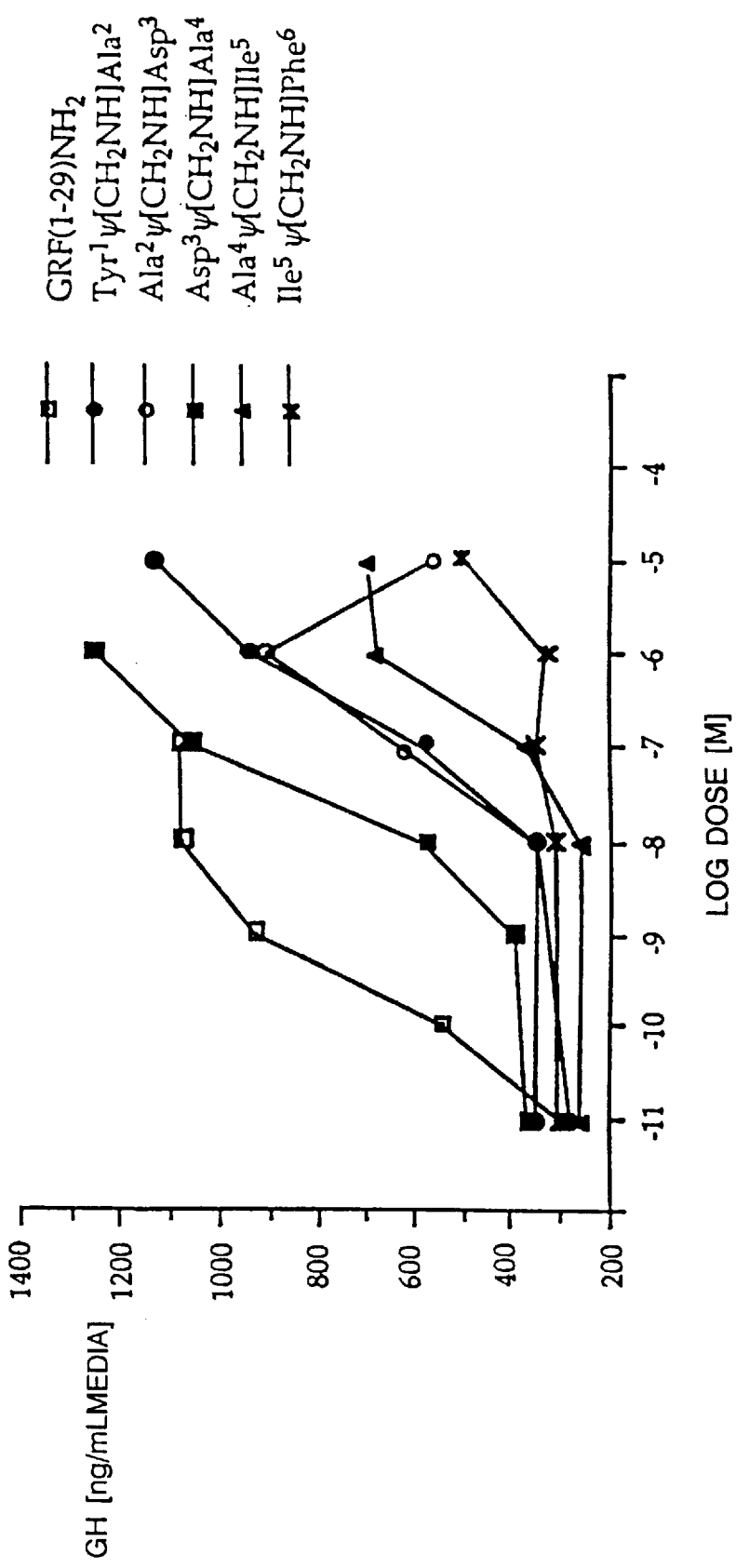
FIGS. 2 and 3 are graphs showing the effect of pseudopeptide bond containing analogs of GRF(1–29)$NH_2$ on GH secretion from dispersed rat pituitary cells.
Figure 3:
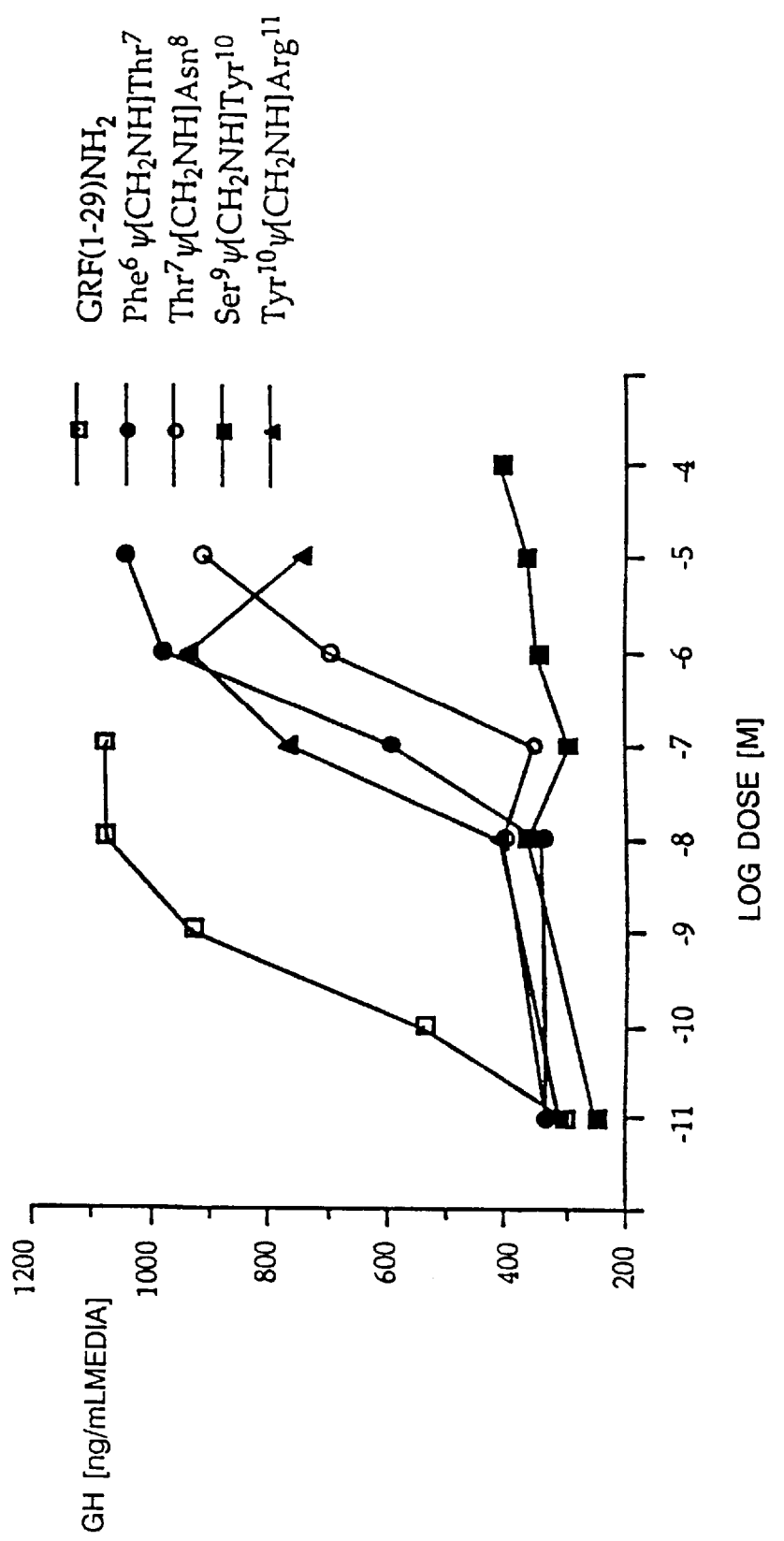
Figure 4:
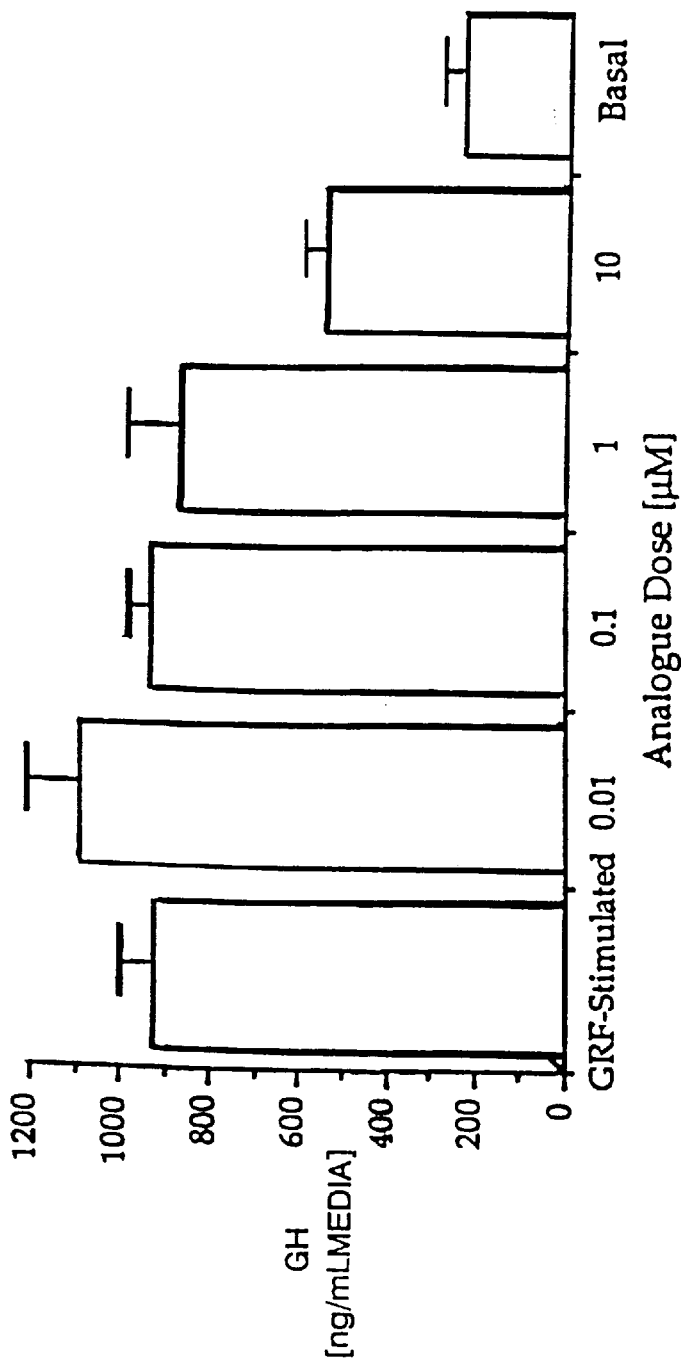
FIG. 4 is a graph showing the antagonism of GRF stimulated GH secretion by $Ser^9\Psi[CH_2NH]Tyr^{10}$GRF (1–29)$NH_2$.

The purified analogs were assayed in a 4-day primary culture of male rat anterior pituitary cells for growth hormone (GH) release, as described by Hocart et al. (1988, supra) and Murphy and Coy (1988, Peptide Research 1:36). Potential antagonists were retested in the presence of GRF (1–29)NH$_2$ (1 nM). The results are shown in FIGS. 2–4, in which different dosages of the analogs were measured against GRF.

The incorporation of the reduced peptide bond isostere in the N-terminal region of GRF(1–29)NH$_2$ produced very weak agonists and one antagonist with an IC$_{50}$ of approximately 10 μM.

Placement of the pseudopeptide bond between the N-terminal 9th and 10th residues produced the analogue [Ser$^9$Ψ[CH$_2$NH]Tyr$^{10}$]- GRF(1–29)NH$_2$ (SEQ ID NO: 5)(peptide VIII). This analog was found to be inactive in the potency assay, and was therefore tested for antagonist activity in the presence of a stimulating dose of GRF(1–29)NH$_2$ (1 nM). The results are shown graphically in FIG. 4. [Ser$^9$Ψ[CH$_2$NH]Tyr$^{10}$]-GRF(1–29)NH$_2$ was found to be an antagonist in the 10 μM range vs 1 nM GRF. Earlier conventional structure-activity studies with the same peptide had elucidated a more potent antagonist, namely [N-Ac—Tyr$^1$, D-Arg$^2$]GRF(1–29)NH$_2$ (Robberecht et al., J. Endocrinology, 1985, 117, 1759). This analog had an IC$_{50}$ of approximately 1 μM in an assay for adenylate cyclase activity in rat anterior pituitary homogenates.

Placement of the pseudopeptide bond in any one position between the remaining N-terminal 11 amino acids produced analogs having less activity than GRF(1–29)NH$_2$. These results are presented in Table 6 (n=number of separate experiments in quadruplicate from which the corresponding curves in the Figures were calculated). Incorporation of the isosteres Tyr$^1$Ψ[CH$_2$NH]Ala$^2$ and Ala$^2$Ψ[CH$_2$NH]Asp$^3$, gave weak agonists with ~0.1 activity of the control (peptide I, Tyr$^1$Ψ [CH$_2$NH]Ala$^2$, 0.12%, and peptide II, Ala$^2$Ψ[CH$_2$NH]Asp$^3$, 0.13%). At position 3, the isostere Asp$^3$Ψ[CH$_2$NH]Ala$^4$ (peptide III) produced the most potent agonist of the series which retained 1.6% of the activity of the control. When Ala$^4$Ψ[CH$_2$NH]Ile$^5$ was incorporated at position 4 (peptide IV), the activity dropped to 0.02% of GRF(1–29)NH$_2$. This drop continued at position 5, where the isostere Ile$^5$Ψ[CH$_2$NH]Phe$^6$ (peptide V) produced the least active agonist with a potency of <0.01% of that of the control. Phe$^6$Ψ[CH$_2$NH]Thr$^7$ (peptide VI) produced a potency to 0.13% of that of GRF(1–29)NH$_2$ but the isostere Thr$^7$Ψ[CH$_2$NH]Asn$^8$ produced a weak agonist (peptide VII, 0.02% potency). With the isostere Ser$^9$Ψ[CH$_2$NH]Tyr$^{10}$ in the peptide (VIII), all trace of agonist activity was lost at doses as high as 0.1 mM. Another agonist was produced with Tyr$^{10}$Ψ[CH$_2$NH]Arg$^{11}$ in the peptide although it too had low potency (IX, 0.39%).

The loss of potency observed after placement of the pseudopeptide bond at each position of the first 11 N-terminal positions of GRF(1–29) was greater than that seen with smaller peptides, such as somatostatin and bombesin which contain β-bends in the region of the molecule important for receptor recognition. Chou-Fasman analysis shows GRF to be predominantly α-helical in character in the biologically important N-terminal portion of the molecule. The replacement of the naturally-occurring C=0 bond by the C=H$_2$ bond of the pseudopeptide bond has pronounced effects on α-helical formation due to a loss of intramolecular H-bonding sites and increased rotational freedom about the isostere C—N bond. Loss of intermolecular H-bonding sites might also induce changes in receptor binding capabilities of both β-bend and α-helical peptides. However, given the dramatic loss in activity of these GRF analogues, as compared to somatostatin and bombesin, effects on peptide conformation are probably more important in the larger helical GRF molecule.

Use

The peptides of the invention may be administered to a mammal, particularly a human, in one of the traditional modes (e.g., orally, parenterally, transdermally, or transmucosally), in a sustained release formulation using a biodegradable biocompatible polymer, or by on-site delivery (e.g., in the case of anti-cancer bombesin to the lungs) using micelles, gels and liposomes.

The bombesin antagonists of the invention are suitable for the treatment of all forms of cancer where bombesin-related substances act as autocrine or paracrine mitotic agents, particularly small-cell lung carcinoma. The peptides can also be used for the inhibition of gastric acid secretion and motility disorders of the GI tract, the symptomatic relief and/or treatment of exocrine pancreatic adenocarcinoma, and the restoration of appetite to cachexic patients. The peptides can be administered to a human patient in a dosage of 0.5 μg/kg/day to 5 mg/kg/day. For some forms of cancer, e.g., small cell lung carcinoma, the preferred dosage for curative treatment is 250 mg/patient/day.

The compound can be administered to a mammal, e.g., a human, in the dosages used for growth hormone releasing factor or, because of their decreased potency, in larger dosages. The compounds can be administred to a mammal, e.g., a human, in a dosage of 0.01 to 1000 mcg/kg/day, preferably 0.1 to 100 mcg/kg/day.

TABLE 1

| Code | Structure | 3T3 GRP Receptor IC50(nM) | Thym. Uptake IC50(nM) |
|---|---|---|---|
| BIM-26092 | Gly-Asn-His-Trp-Ala-Val-Gly-His-Leuψ[CH$_2$NH]Leu-NH$_2$ (SEQ ID NO: 11) Neuromedin C | 242 | 466 |
| BIM-26095 | pGlu-Gln-Trp-Ala-Val-D-Ala-His-Leuψ[CH$_2$NH]Leu-NH$_2$ Litorin | 2623 | 1209 |
| BIM-26100 | pGlu-Gln-Trp-Ala-Val-Gly-His-Pheψ[CH$_2$NH]Leu-NH$_2$ Litorin | 23 | 26 |
| BIM-26101 | pGlu-Gln-Trp-Ala-Val-Gly-His-Leu[CH$_2$NH]Leu-NH$_2$ Litorin | 118 | 296 |
| BIM-26105 | D-Ala-Asn-His-Trp-Ala-Val-D-ALa-His-Leuψ[CH$_2$CH]Leu-NH$_2$ Neuromedin C | 107 | 107 |
| BIM-26106 | desGly-D-Ala-His-Trp-Ala-Val-D-Ala-His-Leuψ[CH$_2$NH]Met-NH$_2$ Neuromedin C | 401 | 354 |
| BIM-26107 | D-Phe-His-Trp-Ala-Val-Gly-His-Leuψ[CH$_2$NH]Leu-NH$_2$ Neuromedin C | 199 | 154 |
| BIM-26108 | N-Ac-D-Ala-His-Trp-Ala-Val-Gly-His-Leuψ[CH$_2$NH]Leu-NH$_2$ GRP (19-27) | 841 | >1000 |
| BIM-26113 | D-Phe-Gln-Trp-Ala-Val-Gly-His-Leuψ[CH$_2$NH]Leu-NH$_2$ Litorin | 5.8 | 9 |
| BIM-26114 | D-Nal-Gln-Trp-Ala-Val-Gly-His-Leuψ[CH$_2$NH]Leu-NH$_2$ Litorin | 23.5 | 28 |
| BIM-26120 | pGlu-Gln-Trp-Ala-Val-Gly-His-Sta-NH$_2$ Litorin | 150 | 165 |
| BIM-26122 | D-Phe-Gln-Trp-Ala-Val-Gly-His-Leu-NH$_2$ Litorin | 5.9 | 28.6 |
| BIM-26136 | D-Nal-Gln-Trp-Ala-Val-Gly-His-Leuψ[CH$_2$NH]Phe-NH$_2$ Litorin | 1.4 | 3.3 |
| BIM-26182 | D-Cpa-Gln-Trp-Ala-Val-Gly-His-β-Leu-NH$_2$ Litorin | 0.88 | 4.77 |

TABLE 2

IN VIVO TUMOR INHIBITORY ACTIVITY OF THE BOMBESIN ANTAGONIST BIM-26100: NCI-H69 HUMAN SCLC

| Group No. | Treatment | Tumor Size[1] Day 18 (mm) | % Test/Control | Tumor Size Day 28 (mm) | % Test/Control |
|---|---|---|---|---|---|
| 1 | Vehicle treated control, 0.2 ml, s.c. inf., b.i.d., QD1–28 | 10.9 ± 1.82 | | 15.9 ± 2.27 | |
| 2 | BIM-26100, 50 µg/inj., s.c., b.i.d., QD1–28 | 10.1 ± 1.47 | 93 | 17.3 ± 1.96 | 108 |
| 3 | BIM-26100, 50 µg/inj., s.c. inf., b.i.d., QD1–28 | 7.6 ± 1.56** | 70 | 13.7 ± 0.67* | 86 |

[1]Data reported as means ± SD on 10 animals in the control and 5 in test groups.
Student's Test significance of difference from control: *p < 0.05; **p = 0.01.

TABLE 3

EFFECT OF TUMOR GROWTH AND BIM-26100 TREATMENT ON BODY WEIGHT: LACK OF SYSTEMIC TOXICITY

| Group No. | Treatment | Body Weight(gm)[1] Day 0 | Body Weight(gm) Day 18 | Body Weight(gm) Day 28 |
|---|---|---|---|---|
| 1 | Vehicle treated control, 0.2 ml, s.c. inf., b.i.d., QD1–28 | 17.3 | 19.6 | 19.7 |
| 2 | BIM-26100, 50 µg/inj., s.c., b.i.d., QD1–28 | 16.9 | 19.2 | 19.1 |
| 3 | BIM-26100, 50 µg/inj., s.c. inf., b.i.d., QD1–28 | 17.7 | 20.4 | 21.1 |

[1]Body weights are presented as means of 10 animals in the control and 5 in test groups:
Tumor weights calculated from 2 largest diameters in mm converted to mgs using the formula for an ellipsoid (length × width $^2$/2)mgs, were subtracted from total body weights.

TABLE 4

Peptide Chromatographic, Purity and Mass Spectral Data

| Peptide | Analogue | HPLC $t_R$ /min | Purity /% | FAB-MS (M-H$^+$) |
|---|---|---|---|---|
| | GRF(1-29)NH$_2$ | 16.9 | 99.4 | |
| I | Tyr$^1$ψ[CH$_2$NH]Ala$^2$ | 16.2 | 99.4 | 3345 |
| II | Ala$^2$ψ[CH$_2$NH]Asp$^3$ | 14.9 | 94.1 | 3345 |
| III | Asp$^3$ψ[CH$_2$NH]Ala$^4$ | 14.4 | 95.5 | 3345 |
| IV | Ala$^4$ψ[CH$_2$NH]Ile$^5$ | 13.6 | 97.6 | 3345 |
| V | Ile$^5$ψ[CH$_2$NH]Phe$^6$ | 14.3 | 97.2 | 3345 |
| VI | Phe$^6$ψ[CH$_2$NH]Thr$^7$ | 14.7 | 95.3 | 33457 |
| VII | Thr$^7$ψ[CH$_2$NH]Asn$^8$ | 14.7 | 96.7 | 3345 |
| VIII | Ser$^9$ψ[CH$_2$NH]Tyr$^{10}$ | 15.8 | 92.6 | 3343 |
| IX | Tyr$^{10}$ψ[CH$_2$NH]Arg$^{11}$ | 13.5 | 97.7 | 3344 |

TABLE 5

5-Amino Acid Analyses

| | GRF-(1–29)NH$_2$ | I | II | III | IV | V | VI | VII | VIII | IX |
|---|---|---|---|---|---|---|---|---|---|---|
| Asp | 3.22 | 3.02 | 1.95 | 1.88 | 2.89 | 2.37 | 3.00 | 1.90 | 2.39 | 3.25 |
| Thr | 1.06 | 1.00 | 0.87 | 0.87 | 1.08 | 0.68 | | | 0.98 | 0.97 |
| Ser | 2.98 | 2.82 | 2.52 | 2.32 | 3.19 | 2.75 | 2.95 | 2.94 | 1.85 | 2.81 |
| Glu | 2.25 | 2.20 | 2.50 | 1.81 | 2.24 | 2.19 | 2.25 | 2.09 | 2.25 | 2.10 |
| Gly | 1.12 | 1.10 | 1.04 | 1.01 | 1.03 | 1.13 | 0.95 | 0.97 | 1.08 | 1.00 |
| Ala | 3.30 | 2.19 | 2.23 | 2.03 | 2.20 | 1.80 | 3.03 | 3.14 | 3.13 | 3.07 |
| Val | 0.75 | 0.97 | 1.00 | 1.00 | 1.00 | 1.00 | 1.00 | 1.00 | 1.00 | 1.00 |
| Met | 0.99 | 1.13 | 1.00 | 0.91 | 0.98 | 1.00 | 1.01 | 0.95 | 0.89 | 0.97 |
| Ile | 1.77 | 1.87 | 1.83 | 1.59 | 1.08 | 1.06 | 1.11 | 1.57 | 1.90 | 1.88 |
| Leu | 4.00 | 4.00 | 3.75 | 2.92 | 4.12 | 4.04 | 4.05 | 3.38 | 4.08 | 4.06 |
| Tyr | 1.92 | 1.11 | 1.65 | 1.73 | 2.04 | 1.23 | 2.02 | 2.00 | 0.94 | 0.92 |
| Phe | 0.70 | 0.91 | 0.94 | 0.86 | 0.90 | | | 0.93 | 0.94 | 1.07 |
| Lys | 2.02 | 1.81 | 1.63 | 2.37 | 2.15 | 2.08 | 1.97 | 2.01 | 2.24 | 1.82 |
| Arg | 3.16 | 2.91 | 2.90 | 2.89 | 3.11 | 3.14 | 3.10 | 3.07 | 3.40 | 2.14 |

TABLE 6

In Vitro Biological Potencies of Reduced Peptide Bond GRF(1-29)NH₂ Analogues

| Peptide | Analogue | Potency (%) | 95% Confidence Interval | n |
|---|---|---|---|---|
|  | GRF(1-29)NH$_2$ | 100 | — | 28 |
| I | Tyr$^1$ψ[CH$_2$NH]Ala$^2$ | 0.12 | 0.07–0.22 | 7 |
| II | Ala$^2$ψ[CH$_2$NH]Asp$^3$ | 0.13 | 0.08–0.24 | 7 |
| III | Asp$^3$ψ[CH$_2$NH]Ala$^4$ | 1.6 | 0.9–3.0 | 4 |
| IV | Ala$^4$ψ[CH$_2$NH]Ile$^5$ | 0.02 | 0.01–0.05 | 4 |
| V | Ile$^5$ψ[CH$_2$NH]Phe$^6$ | <0.01 | n.d. | 7 |
| VI | Phe$^6$ψ[CH$_2$NH]Thr$^7$ | 0.13 | 0.07–0.25 | 7 |
| VII | Thr$^7$ψ[CH$_2$NH]Asn$^8$ | 0.02 | 0.01–0.03 | 4 |
| VIII | Ser$^9$ψ[CH$_2$NH]Tyr$^{10}$ | — | — | 5 |
| IX | Tyr$^{10}$ψ[CH$_2$NH]Arg$^{11}$ | 0.39 | 0.23–0.67 | 6 |

Other embodiments are within the following claims.

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( i x ) FEATURE:
        ( D ) OTHER INFORMATION: The sequence contains at position 1 a pyroglutamate, rather than a glutamate, and has an amide C-terminus (i.e., COyNH2), rather than a carboxyl C-terminus (i.e., COyOH).

( x i ) SEQUENCE DESCRIPTION: SEQ ID NO: 1:

Glu Gln Arg Leu Gly Asn Gln Trp Ala Val Gly His Leu Met
1                      5                                10

( 2 ) INFORMATION FOR SEQ ID NO: 2:

( i ) SEQUENCE CHARACTERISTICS:
        ( A ) LENGTH: 27
        ( B ) TYPE: amino acid
        ( C ) STRANDEDNESS:
        ( D ) TOPOLOGY: linear ( i x ) FEATURE:
        ( D ) OTHER INFORMATION: The sequence has an amide C-terminus (i.e., COyNH2), rather than a carboxyl C-terminus (i.e., COyOH).

( x i ) SEQUENCE DESCRIPTION: SEQ ID NO: 2:

Ala Pro Val Ser Val Gly Gly Gly Thr Val Leu Ala Lys Met Tyr
1                      5                                10                         15

Pro Arg Gly Asn His Trp Ala Val Gly His Leu Met
                    20                                25

( 2 ) INFORMATION FOR SEQ ID NO: 3:

( i ) SEQUENCE CHARACTERISTICS:
        ( A ) LENGTH: 27
        ( B ) TYPE: amino acid
        ( C ) STRANDEDNESS:
        ( D ) TOPOLOGY: linear ( i x ) FEATURE:
  ( D ) OTHER INFORMATION: The sequence has an amide C-
    terminus (i.e., COyNH2), rather than a carboxyl C-
    terminus (i.e., COyOH).

( x i ) SEQUENCE DESCRIPTION: SEQ ID NO: 3:

| Val | Pro | Leu | Pro | Ala | Gly | Gly | Gly | Thr | Val | Leu | Thr | Lys | Met | Tyr |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Pro | Arg | Gly | Asn | His | Trp | Ala | Val | Gly | His | Leu | Met |
|-----|-----|-----|-----|-----|-----|-----|-----|-----|-----|-----|-----|
|     |     |     |     | 20  |     |     |     |     | 25  |     |     |

( 2 ) INFORMATION FOR SEQ ID NO: 4:

( i ) SEQUENCE CHARACTERISTICS:
    ( A ) LENGTH: 8
    ( B ) TYPE: amino acid
    ( C ) STRANDEDNESS:
    ( D ) TOPOLOGY: linear ( i x ) FEATURE:
    ( D ) OTHER INFORMATION: The sequence contains at
      position 1 a pyroglutamate, rather than a glutamate,
      and has an amide C-terminus (i.e., COyNH2), rather
      than a carboxyl C-terminus (i.e., COyOH). Xaa stands for
      statine.

( x i ) SEQUENCE DESCRIPTION: SEQ ID NO: 4:

| Glu | Gln | Trp | Ala | Val | Gly | His | Xaa |
|-----|-----|-----|-----|-----|-----|-----|-----|
| 1   |     |     |     | 5   |     |     |     |

( 2 ) INFORMATION FOR SEQ ID NO: 5:

( i ) SEQUENCE CHARACTERISTICS:
    ( A ) LENGTH: 29
    ( B ) TYPE: amino acid
    ( C ) STRANDEDNESS:
    ( D ) TOPOLOGY: linear ( i x ) FEATURE:
    ( D ) OTHER INFORMATION: The sequence has a
      non- peptidyl
      bond (i.e., CH2yNH), rather than a peptidyl bond
      ( i . e . ,   C O y N H ), between Ser and Tyr, and has an amide C-
      terminus (i.e., COyNH2), rather than a carboxyl C-
      terminus (i.e., COyOH).

( x i ) SEQUENCE DESCRIPTION: SEQ ID NO: 5:

| Tyr | Ala | Asp | Ala | Ile | Phe | Thr | Asn | Ser | Tyr | Arg | Lys | Val | Leu | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Leu | Ser | Ala | Arg | Lys | Leu | Leu | Gln | Asp | Ile | Met | Ser | Arg |
|-----|-----|-----|-----|-----|-----|-----|-----|-----|-----|-----|-----|-----|-----|
|     |     |     |     | 20  |     |     |     |     | 25  |     |     |     |     |

( 2 ) INFORMATION FOR SEQ ID NO: 6:

( i ) SEQUENCE CHARACTERISTICS:
    ( A ) LENGTH: 9
    ( B ) TYPE: amino acid
    ( C ) STRANDEDNESS:
    ( D ) TOPOLOGY: linear ( i x ) FEATURE:
    ( D ) OTHER INFORMATION: The sequence contains at
      position 1 a pyroglutamate, rather than a glutamate,
      has a non- peptidyl bond (i.e., CH2yNH), rather than a
      peptidyl bond (i.e., COyNH), between Phe and Leu, and
      has an amide C-terminus (i.e., COyNH2), rather than a
      carboxyl C- terminus (i.e., COyOH).

( x i ) SEQUENCE DESCRIPTION: SEQ ID NO: 6:

| Glu | Gln | Trp | Ala | Val | Gly | His | Phe | Leu |
|-----|-----|-----|-----|-----|-----|-----|-----|-----|
| 1   |     |     |     | 5   |     |     |     |     |

(2) INFORMATION FOR SEQ ID NO: 7:

(i) SEQUENCE CHARACTERISTICS:
        (A) LENGTH: 9
        (B) TYPE: amino acid
        (C) STRANDEDNESS:
        (D) TOPOLOGY: linear (ix) FEATURE:
        (D) OTHER INFORMATION: The sequence contains at position 1 a pyroglutamate, rather than a glutamate, has a non- peptidyl bond (i.e., CH2yNH), rather than a peptidyl bond (i.e., COyNH), between Leu and Leu, and has an amide C-terminus (i.e., COyNH2), rather than a carboxyl C- terminus (i.e., COyOH).

(xi) SEQUENCE DESCRIPTION: SEQ ID NO: 7:

Glu Gln Trp Ala Val Gly His Leu Leu
1               5

(2) INFORMATION FOR SEQ ID NO: 8:

(i) SEQUENCE CHARACTERISTICS:
        (A) LENGTH: 8
        (B) TYPE: amino acid
        (C) STRANDEDNESS:
        (D) TOPOLOGY: linear (ix) FEATURE:
        (D) OTHER INFORMATION: The sequence contains at position 1 a pyroglutamate, rather than a glutamate, and has an methylester C-terminus (i.e., COyOCH3), rather than a carboxyl C-terminus (i.e., COyOH).

(xi) SEQUENCE DESCRIPTION: SEQ ID NO: 8:

Glu Gln Trp Ala Val Gly His Phe
1               5

(2) INFORMATION FOR SEQ ID NO: 9:

(i) SEQUENCE CHARACTERISTICS:
        (A) LENGTH: 8
        (B) TYPE: amino acid
        (C) STRANDEDNESS:
        (D) TOPOLOGY: linear (ix) FEATURE:
        (D) OTHER INFORMATION: The sequence contains at position 1 a pyroglutamate, rather than a glutamate, and has an methylester C-terminus (i.e., COyOCH3), rather than a carboxyl C-terminus (i.e., COyOH).

(xi) SEQUENCE DESCRIPTION: SEQ ID NO: 9:

Glu Gln Trp Ala Val Gly His Leu
1               5

(2) INFORMATION FOR SEQ ID NO: 10:

(i) SEQUENCE CHARACTERISTICS:
        (A) LENGTH: 35
        (B) TYPE: amino acid
        (C) STRANDEDNESS:
        (D) TOPOLOGY: linear (ix) FEATURE:
        (D) OTHER INFORMATION: Tyr at position 1 and Leu at position 35 are covalently linked to a t-butyloxycarbonyl group ("Boc") and a methylbenzhydrylamine group, respectively.

(xi) SEQUENCE DESCRIPTION: SEQ ID NO: 10:

```
Tyr  Arg  Lys  Ala  Leu  Gly  Gln  Leu  Ser  Ala  Arg  Lys  Leu  Leu  Gln  Asp
 1                   5                        10                        15
Ile  Met  Ser  Arg  Gln  Gln  Gly  Glu  Ser  Asn  Gln  Glu  Arg  Gly  Ala  Arg
               20                       25                        30
Ala  Arg  Leu
           35
```

( 2 ) INFORMATION FOR SEQ ID NO: 11:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: The sequence has a
        non- peptidyl
        bond (i.e., CH2yNH), rather than a peptidyl bond
        ( i . e . , C O y N H ), between Leu and Leu, and also has an amide
        C- terminus (i.e., COyNH2), rather than a carboxyl C-
        terminus (i.e., COyOH).

( x i ) SEQUENCE DESCRIPTION: SEQ ID NO: 11:

```
Gly  Asn  His  Trp  Ala  Val  Gly  His  Leu  Leu
 1                   5                        10
```

7 7 4 6 . B 1 1

---

We claim:

1. A therapeutic peptide said peptide being an analog of one of the following naturally occurring peptides terminating at the carboxy-terminus with a Met residue: (a) litorin; (b) the ten amino acid carboxy-terminal region of mammalian gastrin releasing peptide; and (c) the ten amino acid carboxy-terminal region of amphibian bombesin; said therapeutic peptide being of the formula:

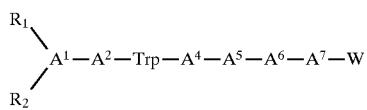

wherein $A^1$=the D-isomer of any of p-X-Phe (where X=F, Cl, Br, $NO_2$, OH, H, or $CH_3$), Trp, or β-Nal;

$A^2$=Gly, Ala, Val, Gln, Asn, Leu, Ile, Met, p-X-Phe (where X=F, Cl, Br, $NO_2$, OH, H, or $CH_3$), Trp, Cys, β-Nal, His, 1-methyl-His, or 3-methyl-His;

$A^4$=Ala, Val, Gln, Asn, Gly, Leu, Ile, Nle, α-aminobutyric acid, Met, p-X-Phe (where X=F, Cl, Br, $NO_2$, OH, H, or $CH_3$), Trp, Cys, or β-Nal;

$A^5$=Gln, Asn, Gly, Ala, Leu, Ile, Nle, α-aminobutyric acid, Met, Val, p-X-Phe (where X=F, Cl, Br, OH, H, or $CH_3$), Trp, Thr, or β-Nal;

$A^6$=Sar, Gly, or the D-isomer or any of Ala, N—methyl-Ala, Val, Gln, Asn, Leu, Ile, Met, p-X-Phe (where X=F, Cl, Br, $NO_2$, OH, H, or $CH_3$), Trp, Cys, or β-Nal;

$A^7$=1-methyl-His, 3-methyl-His, or His; provided that W is $$\begin{array}{c} R_3 \quad Z_1 \quad\quad Z_2 \quad O \\ | \quad\quad | \quad\quad\quad | \quad\quad || \\ N-CH-R_4-CH-C-V, \end{array} \quad (I)$$

wherein $R_4$ is $CH_2$—NH, and each $Z_1$ and $Z_2$, independently, is the identifying group of any one of the amino acids Gly, Ala, Val, Leu, Ile, Ser, Asp, Asn, Glu, Gln, p-X-Phe (where X=H, F, Cl, Br, $NO_2$, OH, or $CH_3$), Trp, Cys, Met, Pro, HyPro, or cylcohexyl-Ala;

and V is either $OR_5$ or

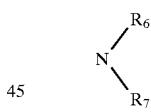

where each $R_3$, $R_5$, $R_6$, and $R_7$, independently, is H, lower alkyl, lower phenylalkyl, or lower naphthylalkyl; further provided that, for formula (I), any asymmetric carbon atom can be R, S or a racemic mixture; and further provided that each $R_1$ and $R_2$, independently, is H, $C_{1-12}$ alkyl, $C_{7-10}$ phenylalkyl, or $COE_1$ (where $E_1$ is $C_{1-20}$ alkyl, $C_{3-20}$ alkenyl, $C_{3-20}$ alkynyl, phenyl, naphthyl, or $C_{7-10}$ phenylalkyl), and $R_1$ and $R_2$ are bonded to the N-terminal amino acid of said peptide, and further provided that when one of $R_1$ or $R_2$ is $COE_1$, the other must be H, or a pharmaceutically acceptable salt thereof.

2. The therapeutic peptide of claim 1 wherein $A^1$=D-Phe, D-β-Nal, or D-Cpa;

$A^2$=Gln, His, 1-methyl-His, or 3-methyl-His;

$A^4$=Ala;

$A^5$=Val;

$A^6$=Sar, Gly,or D—Ala;

$A^7$=His;

and, $Z_1$ is the identifying group of Leu, or Phe, and $Z_2$ is the identifying group of Leu or Phe.

3. The therapeutic peptide of claim 2 of the formula:

D-β-Nal—Gln—Trp—Ala—Val—Gly—His—LeuΨ[CH$_2$NH]Phe—NH$_2$.

4. The therapeutic peptide of claim 2 wherein W is (II), $R_4$ is CH$_2$—NH, and said carbon atom bonded to $Z_2$ is of said R configuration.

5. The therapeutic peptide of claim 4 of the formula:

D—Phe—Gln—Trp—Ala—Val—Gly—His—LeuΨ[CH$_2$NH]—D—Phe—NH$_2$.

* * * * *